(12) United States Patent
Katra et al.

(10) Patent No.: US 9,615,757 B2
(45) Date of Patent: Apr. 11, 2017

(54) METHOD AND APPARATUS FOR REMOTE DETECTION AND MONITORING OF FUNCTIONAL CHRONOTROPIC INCOMPETENCE

(71) Applicant: Corventis, Inc., Saint Paul, MN (US)

(72) Inventors: Rodolphe Katra, Blaine, MN (US); Niranjan Chakravarthy, Eden Prairie, MN (US); Imad Libbus, Saint Paul, MN (US)

(73) Assignee: Medtronic Monitoring, Inc., San Jose, CA (US)

( * ) Notice: Subject to any disclaimer, the term of this patent is extended or adjusted under 35 U.S.C. 154(b) by 172 days.

(21) Appl. No.: 14/310,105

(22) Filed: Jun. 20, 2014

(65) Prior Publication Data

US 2014/0371604 A1    Dec. 18, 2014

Related U.S. Application Data

(63) Continuation of application No. 12/910,076, filed on Oct. 22, 2010, now Pat. No. 8,790,259.
(Continued)

(51) Int. Cl.
*A61B 5/08* (2006.01)
*A61B 5/0245* (2006.01)
(Continued)

(52) U.S. Cl.
CPC .......... *A61B 5/0245* (2013.01); *A61B 5/0002* (2013.01); *A61B 5/0205* (2013.01);
(Continued)

(58) Field of Classification Search
None
See application file for complete search history.

(56) References Cited

U.S. PATENT DOCUMENTS 834,261 A    10/1906  Chambers
2,087,124 A   7/1937  Smith et al.
(Continued)

OTHER PUBLICATIONS

Azarbal B, Hayes SW, Lewin HC, Hachamovitch R, Cohen I, Berman DS. The incremental prognostic value of percentage of heart rate reserve achieved over myocardial perfusion single-photon emission computed tomography in the prediction of cardiac death and all-cause mortality: Superiority over 85% of maximal age-predicted heart rate. J Am Coll Cardiol.*

*Primary Examiner* — Michael Kahelin
*Assistant Examiner* — Mitchell E Alter
(74) *Attorney, Agent, or Firm* — Billion & Armitage; Michael A. Collins

(57) ABSTRACT

Methods and apparatus to determine the presence of and track functional chronotropic incompetence (hereinafter "CI") in an in-home setting under conditions of daily living. The functional CI of the patient may be determined with one or more of a profile of measured patient heart rates, a measured maximum patient heart rate, or a peak of the heart rate profile. The functional CI of the patient may be determined with the measured heart rate profile, in which the measured heart rate profile may correspond to heart rates substantially less than the maximum heart rate of the patient, such that the heart rate can be safely measured when the patient is remote from a health care provider. The functional CI of the patient may be determined based a peak of the remotely measured heart rate profile, for example a peak corresponding to the mode of the heart rate distribution profile.

10 Claims, 18 Drawing Sheets

200- Method of monitoring a patient
205- Adhere measurement device to patient to measure heart rate, activity, body posture, respiration rate and bioimpedance
210- Measure, store and process patient data with adherent device
212- Determine patient drug treatment
215- Transmit patient data from adherent device to gateway
220- Receive patient data with gateway
225- Measure, store and process patient data with gateway
230- Transmit patient data from gateway to remote server
235- Measure, store and process patient data with remote server
240- Identify CI with profile of remote heart rates
    241- determine profile of remote heart rates
    242- determine peak of profile of remote heart rates
    243- determine portion of profile above peak
    244- determine portion of profile below peak
    245- compare portion above peak to portion below peak
    246- identify CI when portion above peak is less than portion below
250- Identify CI with resting remote HR
    251- determine occurrence of heart rates corresponding to profile
    252- determine peak of the remote heart rates
    254- determine remote resting HR based on peak of remote HR
    255- determine age corrected maximum HR
    256- determine HRR based on age corrected maximum HR and remote resting HR
    257- identify CI when HRR below threshold
260- Identify CI with maximum HR
    261- determine threshold activity amount based on patient data from a plurality of other patients
    262- determine patient activity above threshold
    263- determine heart rates corresponding to patient activity above threshold
    264- determine correlation of HR above threshold with one or more of activity, body posture, respiration rate and bioimpedance
    265- determine patient drug treatment and compliance
    266- determine CI based on patient drug treatment and correlation of HR above threshold with the one or more of one or more of activity, body posture, respiration rate and bioimpedance
270- Transmit notification to one or more of physician or patient based on identification of CI

Related U.S. Application Data

(60) Provisional application No. 61/253,866, filed on Oct. 22, 2009.

(51) Int. Cl.
  A61B 5/00      (2006.01)
  A61B 5/0205   (2006.01)
  A61B 5/053    (2006.01)
  A61B 5/11     (2006.01)

(52) U.S. Cl.
  CPC .............. *A61B 5/0537* (2013.01); *A61B 5/08* (2013.01); *A61B 5/0816* (2013.01); *A61B 5/1116* (2013.01); *A61B 5/1118* (2013.01); *A61B 2560/0412* (2013.01)

(56) References Cited

U.S. PATENT DOCUMENTS

| | | |
|---|---|---|
| 2,184,511 A | 12/1939 | Bagno et al. |
| 3,170,459 A | 2/1965 | Phipps et al. |
| 3,232,291 A | 2/1966 | Parker |
| 3,370,459 A | 2/1968 | Cescati |
| 3,517,999 A | 6/1970 | Weaver |
| 3,620,216 A | 11/1971 | Szymanski |
| 3,677,260 A | 7/1972 | Funfstuck et al. |
| 3,805,769 A | 4/1974 | Sessions |
| 3,845,757 A | 11/1974 | Wyer |
| 3,874,368 A | 4/1975 | Asrican |
| 3,882,853 A | 5/1975 | Gofman et al. |
| 3,942,517 A | 3/1976 | Bowles et al. |
| 3,972,329 A | 8/1976 | Kaufman |
| 4,008,712 A | 2/1977 | Nyboer |
| 4,024,312 A | 5/1977 | Korpman |
| 4,077,406 A | 3/1978 | Sandhage et al. |
| 4,121,573 A | 10/1978 | Crovella et al. |
| 4,141,366 A | 2/1979 | Cross, Jr. et al. |
| RE30,101 E | 9/1979 | Kubicek et al. |
| 4,185,621 A | 1/1980 | Morrow |
| 4,216,462 A | 8/1980 | DiGaicomo et al. |
| 4,300,575 A | 11/1981 | Wilson |
| 4,308,872 A | 1/1982 | Watson et al. |
| 4,358,678 A | 11/1982 | Lawrence |
| 4,409,983 A | 10/1983 | Albert |
| 4,450,527 A | 5/1984 | Sramek |
| 4,451,254 A | 5/1984 | Dinius et al. |
| 4,478,223 A | 10/1984 | Allor |
| 4,498,479 A | 2/1985 | Martio et al. |
| 4,522,211 A | 6/1985 | Bare et al. |
| 4,661,103 A | 4/1987 | Harman |
| 4,664,129 A | 5/1987 | Helzel et al. |
| 4,669,480 A | 6/1987 | Hoffman |
| 4,673,387 A | 6/1987 | Phillips et al. |
| 4,681,118 A | 7/1987 | Asai et al. |
| 4,692,685 A | 9/1987 | Blaze |
| 4,699,146 A | 10/1987 | Sieverding |
| 4,721,110 A | 1/1988 | Lampadius |
| 4,730,611 A | 3/1988 | Lamb |
| 4,781,200 A | 11/1988 | Baker |
| 4,793,362 A | 12/1988 | Tedner |
| 4,838,273 A | 6/1989 | Cartmell |
| 4,838,279 A | 6/1989 | Fore |
| 4,850,370 A | 7/1989 | Dower |
| 4,880,004 A | 11/1989 | Baker, Jr. et al. |
| 4,895,163 A | 1/1990 | Libke et al. |
| 4,911,175 A | 3/1990 | Shizgal |
| 4,945,916 A | 8/1990 | Kretschmer et al. |
| 4,955,381 A | 9/1990 | Way et al. |
| 4,966,158 A | 10/1990 | Honma et al. |
| 4,981,139 A | 1/1991 | Pfohl |
| 4,988,335 A | 1/1991 | Prindle et al. |
| 4,989,612 A | 2/1991 | Fore |
| 5,001,632 A | 3/1991 | Hall-Tipping |
| 5,012,810 A | 5/1991 | Strand |
| 5,025,791 A | 6/1991 | Niwa |
| 5,027,824 A | 7/1991 | Dougherty et al. |
| 5,050,612 A | 9/1991 | Matsumura |
| 5,063,937 A | 11/1991 | Ezenwa et al. |
| 5,080,099 A | 1/1992 | Way et al. |
| 5,083,563 A | 1/1992 | Collins |
| 5,086,781 A | 2/1992 | Bookspan |
| 5,113,869 A | 5/1992 | Nappholz et al. |
| 5,125,412 A | 6/1992 | Thornton |
| 5,133,355 A | 7/1992 | Strand et al. |
| 5,140,985 A | 8/1992 | Schroeder et al. |
| 5,150,708 A | 9/1992 | Brooks |
| 5,168,874 A | 12/1992 | Segalowitz |
| 5,226,417 A | 7/1993 | Swedlow et al. |
| 5,241,300 A | 8/1993 | Buschmann |
| 5,257,627 A | 11/1993 | Rapoport |
| 5,271,411 A | 12/1993 | Ripley et al. |
| 5,273,532 A | 12/1993 | Niezink et al. |
| 5,282,840 A | 2/1994 | Hudrlik |
| 5,291,013 A | 3/1994 | Nafarrate et al. |
| 5,297,556 A | 3/1994 | Shankar |
| 5,301,677 A | 4/1994 | Hsung |
| 5,319,363 A | 6/1994 | Welch et al. |
| 5,331,966 A | 7/1994 | Bennett et al. |
| 5,335,664 A | 8/1994 | Nagashima |
| 5,343,869 A | 9/1994 | Pross et al. |
| 5,353,793 A | 10/1994 | Bornn |
| 5,362,069 A | 11/1994 | Hall-Tipping |
| 5,375,604 A | 12/1994 | Kelly et al. |
| 5,411,530 A | 5/1995 | Akhtar |
| 5,437,285 A | 8/1995 | Verrier et al. |
| 5,443,073 A | 8/1995 | Wang et al. |
| 5,449,000 A | 9/1995 | Libke et al. |
| 5,450,845 A | 9/1995 | Axelgaard |
| 5,454,377 A | 10/1995 | Dzwonczyk et al. |
| 5,464,012 A | 11/1995 | Falcone |
| 5,469,859 A | 11/1995 | Tsoglin et al. |
| 5,482,036 A | 1/1996 | Diab et al. |
| 5,496,361 A | 3/1996 | Moberg et al. |
| 5,503,157 A | 4/1996 | Sramek |
| 5,511,548 A | 4/1996 | Riazzi |
| 5,511,553 A | 4/1996 | Segalowitz |
| 5,518,001 A | 5/1996 | Snell |
| 5,523,742 A | 6/1996 | Simkins et al. |
| 5,529,072 A | 6/1996 | Sramek |
| 5,544,661 A | 8/1996 | Davis et al. |
| 5,558,638 A | 9/1996 | Evers et al. |
| 5,560,368 A | 10/1996 | Berger |
| 5,564,429 A | 10/1996 | Bornn et al. |
| 5,564,434 A | 10/1996 | Halperin et al. |
| 5,566,671 A | 10/1996 | Lyons |
| 5,575,284 A | 11/1996 | Athan et al. |
| 5,607,454 A | 3/1997 | Cameron et al. |
| 5,632,272 A | 5/1997 | Diab et al. |
| 5,634,468 A | 6/1997 | Platt et al. |
| 5,642,734 A | 7/1997 | Ruben et al. |
| 5,673,704 A | 10/1997 | Marchlinski et al. |
| 5,678,562 A | 10/1997 | Sellers |
| 5,687,717 A | 11/1997 | Halpern et al. |
| 5,718,234 A | 2/1998 | Warden et al. |
| 5,718,235 A * | 2/1998 | Golosarsky .......... A61B 5/0205 600/510 |
| 5,724,025 A | 3/1998 | Tavori |
| 5,738,107 A | 4/1998 | Martinsen et al. |
| 5,748,103 A | 5/1998 | Flach et al. |
| 5,767,791 A | 6/1998 | Stoop et al. |
| 5,769,793 A | 6/1998 | Pincus et al. |
| 5,772,508 A | 6/1998 | Sugita et al. |
| 5,772,586 A | 6/1998 | Heinonen et al. |
| 5,778,882 A | 7/1998 | Raymond et al. |
| 5,788,643 A | 8/1998 | Feldman |
| 5,803,915 A | 9/1998 | Kremenchugsky et al. |
| 5,807,272 A | 9/1998 | Kun et al. |
| 5,814,079 A | 9/1998 | Kieval |
| 5,817,035 A | 10/1998 | Sullivan |
| 5,833,603 A | 11/1998 | Kovacs et al. |
| 5,836,990 A | 11/1998 | Li |
| 5,855,614 A | 1/1999 | Stevens et al. |
| 5,860,860 A | 1/1999 | Clayman |
| 5,862,802 A | 1/1999 | Bird |

(56) References Cited

U.S. PATENT DOCUMENTS

| | | |
|---|---|---|
| 5,862,803 A | 1/1999 | Besson et al. |
| 5,865,733 A | 2/1999 | Malinouskas et al. |
| 5,876,353 A | 3/1999 | Riff |
| 5,904,708 A | 5/1999 | Goedeke |
| 5,935,079 A | 8/1999 | Swanson et al. |
| 5,941,831 A | 8/1999 | Turcott |
| 5,944,659 A | 8/1999 | Flach et al. |
| 5,949,636 A | 9/1999 | Johnson et al. |
| 5,957,854 A | 9/1999 | Besson et al. |
| 5,957,861 A | 9/1999 | Combs et al. |
| 5,964,703 A | 10/1999 | Goodman et al. |
| 5,970,986 A | 10/1999 | Bolz et al. |
| 5,984,102 A | 11/1999 | Tay |
| 5,987,352 A | 11/1999 | Klein et al. |
| 6,007,532 A | 12/1999 | Netherly |
| 6,027,523 A | 2/2000 | Schmieding |
| 6,045,513 A | 4/2000 | Stone et al. |
| 6,047,203 A | 4/2000 | Sackner et al. |
| 6,047,259 A | 4/2000 | Campbell et al. |
| 6,049,730 A | 4/2000 | Kristbjarnarson |
| 6,050,267 A | 4/2000 | Nardella et al. |
| 6,050,951 A | 4/2000 | Friedman et al. |
| 6,052,615 A | 4/2000 | Feild et al. |
| 6,080,106 A | 6/2000 | Lloyd et al. |
| 6,081,735 A | 6/2000 | Diab et al. |
| 6,095,991 A | 8/2000 | Krausman et al. |
| 6,102,856 A | 8/2000 | Groff et al. |
| 6,104,949 A | 8/2000 | Pitts et al. |
| 6,112,224 A | 8/2000 | Peifer et al. |
| 6,117,077 A | 9/2000 | Del Mar et al. |
| 6,125,297 A | 9/2000 | Siconolfi |
| 6,129,744 A | 10/2000 | Boute et al. |
| 6,141,575 A | 10/2000 | Price |
| 6,144,878 A | 11/2000 | Schroeppel et al. |
| 6,164,284 A | 12/2000 | Schulman et al. |
| 6,181,963 B1 | 1/2001 | Chin et al. |
| 6,185,452 B1 | 2/2001 | Schulman et al. |
| 6,190,313 B1 | 2/2001 | Hinkle |
| 6,190,324 B1 | 2/2001 | Kieval et al. |
| 6,198,394 B1 | 3/2001 | Jacobsen et al. |
| 6,198,955 B1 | 3/2001 | Axelgaard et al. |
| 6,208,894 B1 | 3/2001 | Schulman et al. |
| 6,212,427 B1 | 4/2001 | Hoover |
| 6,213,942 B1 | 4/2001 | Flach et al. |
| 6,225,901 B1 | 5/2001 | Kail, IV |
| 6,245,021 B1 | 6/2001 | Stampfer |
| 6,259,939 B1 | 7/2001 | Rogel |
| 6,272,377 B1 | 8/2001 | Sweeney et al. |
| 6,277,078 B1 | 8/2001 | Porat et al. |
| 6,287,252 B1 | 9/2001 | Lugo |
| 6,289,238 B1 | 9/2001 | Besson et al. |
| 6,290,646 B1 | 9/2001 | Cosentino et al. |
| 6,295,466 B1 | 9/2001 | Ishikawa et al. |
| 6,305,943 B1 | 10/2001 | Pougatchev et al. |
| 6,306,088 B1 | 10/2001 | Krausman et al. |
| 6,308,094 B1 | 10/2001 | Shusterman et al. |
| 6,312,378 B1 | 11/2001 | Bardy |
| 6,315,721 B2 | 11/2001 | Schulman et al. |
| 6,327,487 B1 | 12/2001 | Stratbucker |
| 6,336,903 B1 | 1/2002 | Bardy |
| 6,339,722 B1 | 1/2002 | Heethaar et al. |
| 6,343,140 B1 | 1/2002 | Brooks |
| 6,347,245 B1 | 2/2002 | Lee et al. |
| 6,358,208 B1 | 3/2002 | Lang et al. |
| 6,385,473 B1 | 5/2002 | Haines et al. |
| 6,398,727 B1 | 6/2002 | Bui et al. |
| 6,400,982 B2 | 6/2002 | Sweeney et al. |
| 6,411,853 B1 | 6/2002 | Millot et al. |
| 6,416,471 B1 | 7/2002 | Kumar et al. |
| 6,442,422 B1 | 8/2002 | Duckert |
| 6,450,820 B1 | 9/2002 | Palsson et al. |
| 6,450,953 B1 | 9/2002 | Place et al. |
| 6,453,186 B1 | 9/2002 | Lovejoy et al. |
| 6,454,707 B1 | 9/2002 | Casscells, III et al. |
| 6,454,708 B1 | 9/2002 | Ferguson et al. |
| 6,459,930 B1 | 10/2002 | Takehara et al. |
| 6,463,328 B1 | 10/2002 | John |
| 6,473,640 B1 | 10/2002 | Erlebacher |
| 6,480,733 B1 | 11/2002 | Turcott |
| 6,480,734 B1 | 11/2002 | Zhang et al. |
| 6,490,478 B1 | 12/2002 | Zhang et al. |
| 6,491,647 B1 | 12/2002 | Bridger et al. |
| 6,494,829 B1 | 12/2002 | New, Jr. et al. |
| 6,512,949 B1 | 1/2003 | Combs et al. |
| 6,520,967 B1 | 2/2003 | Cauthen |
| 6,527,711 B1 | 3/2003 | Stivoric et al. |
| 6,527,729 B1 | 3/2003 | Turcott |
| 6,544,173 B2 | 4/2003 | West et al. |
| 6,544,174 B2 | 4/2003 | West et al. |
| 6,551,251 B2 | 4/2003 | Zuckerwar et al. |
| 6,551,252 B2 | 4/2003 | Sackner et al. |
| 6,569,160 B1 | 5/2003 | Goldin et al. |
| 6,572,557 B2 | 6/2003 | Tchou et al. |
| 6,572,636 B1 | 6/2003 | Hagen et al. |
| 6,577,139 B2 | 6/2003 | Cooper |
| 6,577,893 B1 | 6/2003 | Besson et al. |
| 6,577,897 B1 | 6/2003 | Shurubura et al. |
| 6,579,231 B1 | 6/2003 | Phipps |
| 6,580,942 B1 | 6/2003 | Willshire |
| 6,584,343 B1 | 6/2003 | Ransbury et al. |
| 6,587,715 B2 | 7/2003 | Singer |
| 6,589,170 B1 | 7/2003 | Flach et al. |
| 6,595,927 B2 | 7/2003 | Pitts-Crick et al. |
| 6,595,929 B2 | 7/2003 | Stivoric et al. |
| 6,600,949 B1 | 7/2003 | Turcott |
| 6,602,201 B1 | 8/2003 | Hepp et al. |
| 6,605,038 B1 | 8/2003 | Teller et al. |
| 6,611,705 B2 | 8/2003 | Hopman et al. |
| 6,611,783 B2 | 8/2003 | Kelly et al. |
| 6,616,606 B1 | 9/2003 | Petersen et al. |
| 6,622,042 B1 | 9/2003 | Thacker |
| 6,636,754 B1 | 10/2003 | Baura et al. |
| 6,641,542 B2 | 11/2003 | Cho et al. |
| 6,645,153 B2 | 11/2003 | Kroll et al. |
| 6,649,829 B2 | 11/2003 | Garber et al. |
| 6,650,917 B2 | 11/2003 | Diab et al. |
| 6,658,300 B2 | 12/2003 | Govari et al. |
| 6,659,947 B1 | 12/2003 | Carter et al. |
| 6,659,949 B1 | 12/2003 | Lang et al. |
| 6,687,540 B2 | 2/2004 | Marcovecchio |
| 6,697,658 B2 | 2/2004 | Al-Ali |
| RE38,476 E | 3/2004 | Diab et al. |
| 6,699,200 B2 | 3/2004 | Cao et al. |
| 6,701,271 B2 | 3/2004 | Willner et al. |
| 6,714,813 B2 | 3/2004 | Ishigooka et al. |
| RE38,492 E | 4/2004 | Diab et al. |
| 6,721,594 B2 | 4/2004 | Conley et al. |
| 6,728,572 B2 | 4/2004 | Hsu et al. |
| 6,748,269 B2 | 6/2004 | Thompson et al. |
| 6,749,566 B2 | 6/2004 | Russ |
| 6,751,498 B1 | 6/2004 | Greenberg et al. |
| 6,760,617 B2 | 7/2004 | Ward et al. |
| 6,773,396 B2 | 8/2004 | Flach et al. |
| 6,775,566 B2 | 8/2004 | Nissila et al. |
| 6,790,178 B1 | 9/2004 | Mault et al. |
| 6,795,722 B2 | 9/2004 | Sheraton et al. |
| 6,814,706 B2 | 11/2004 | Barton et al. |
| 6,816,744 B2 | 11/2004 | Garfield et al. |
| 6,821,249 B2 | 11/2004 | Casscells et al. |
| 6,824,515 B2 | 11/2004 | Suorsa et al. |
| 6,827,690 B2 | 12/2004 | Bardy |
| 6,829,503 B2 | 12/2004 | Alt |
| 6,858,006 B2 | 2/2005 | MacCarter et al. |
| 6,871,211 B2 | 3/2005 | Labounty et al. |
| 6,878,121 B2 | 4/2005 | Krausman et al. |
| 6,879,850 B2 | 4/2005 | Kimball |
| 6,881,191 B2 | 4/2005 | Oakley et al. |
| 6,887,201 B2 | 5/2005 | Bardy |
| 6,890,096 B2 | 5/2005 | Tokita et al. |
| 6,893,396 B2 | 5/2005 | Schulze et al. |
| 6,894,204 B2 | 5/2005 | Dunshee |
| 6,906,530 B2 | 6/2005 | Geisel |
| 6,912,414 B2 | 6/2005 | Tong |
| 6,936,006 B2 | 8/2005 | Sabra |

(56) References Cited

U.S. PATENT DOCUMENTS

| | | |
|---|---|---|
| 6,940,403 B2 | 9/2005 | Kail |
| 6,942,622 B1 | 9/2005 | Turcott |
| 6,952,695 B1 | 10/2005 | Trinks et al. |
| 6,970,742 B2 | 11/2005 | Mann et al. |
| 6,972,683 B2 | 12/2005 | Lestienne et al. |
| 6,978,177 B1 | 12/2005 | Chen et al. |
| 6,980,851 B2 | 12/2005 | Zhu et al. |
| 6,980,852 B2 | 12/2005 | Jersey-Willuhn et al. |
| 6,985,078 B2 | 1/2006 | Suzuki et al. |
| 6,987,965 B2 | 1/2006 | Ng et al. |
| 6,988,989 B2 | 1/2006 | Weiner et al. |
| 6,993,378 B2 | 1/2006 | Wiederhold et al. |
| 6,997,879 B1 | 2/2006 | Turcott |
| 7,003,346 B2 | 2/2006 | Singer |
| 7,018,338 B2 | 3/2006 | Vetter et al. |
| 7,020,508 B2 | 3/2006 | Stivoric et al. |
| 7,027,862 B2 | 4/2006 | Dahl et al. |
| 7,041,062 B2 | 5/2006 | Friedrichs et al. |
| 7,044,911 B2 | 5/2006 | Drinan et al. |
| 7,047,067 B2 | 5/2006 | Gray et al. |
| 7,050,846 B2 | 5/2006 | Sweeney et al. |
| 7,054,679 B2 | 5/2006 | Hirsh |
| 7,059,767 B2 | 6/2006 | Tokita et al. |
| 7,088,242 B2 | 8/2006 | Aupperle et al. |
| 7,113,826 B2 | 9/2006 | Henry et al. |
| 7,118,531 B2 | 10/2006 | Krill |
| 7,127,370 B2 | 10/2006 | Kelly et al. |
| 7,129,836 B2 | 10/2006 | Lawson et al. |
| 7,130,396 B2 | 10/2006 | Rogers et al. |
| 7,130,679 B2 | 10/2006 | Parsonnet et al. |
| 7,133,716 B2 | 11/2006 | Kraemer et al. |
| 7,136,697 B2 | 11/2006 | Singer |
| 7,136,703 B1 | 11/2006 | Cappa et al. |
| 7,142,907 B2 | 11/2006 | Xue et al. |
| 7,149,574 B2 | 12/2006 | Yun et al. |
| 7,149,773 B2 | 12/2006 | Haller et al. |
| 7,153,262 B2 | 12/2006 | Stivoric et al. |
| 7,156,807 B2 | 1/2007 | Carter et al. |
| 7,156,808 B2 | 1/2007 | Quy et al. |
| 7,160,252 B2 | 1/2007 | Cho et al. |
| 7,160,253 B2 | 1/2007 | Nissila |
| 7,166,063 B2 | 1/2007 | Rahman et al. |
| 7,167,743 B2 | 1/2007 | Heruth et al. |
| 7,184,821 B2 | 2/2007 | Belalcazar et al. |
| 7,191,000 B2 | 3/2007 | Zhu et al. |
| 7,194,306 B1 | 3/2007 | Turcott |
| 7,206,630 B1 | 4/2007 | Tarler |
| 7,212,849 B2 | 5/2007 | Zhang et al. |
| 7,215,984 B2 | 5/2007 | Doab et al. |
| 7,215,991 B2 | 5/2007 | Besson et al. |
| 7,238,159 B2 | 7/2007 | Banet et al. |
| 7,248,916 B2 | 7/2007 | Bardy |
| 7,251,524 B1 | 7/2007 | Hepp et al. |
| 7,257,438 B2 | 8/2007 | Kinast |
| 7,261,690 B2 | 8/2007 | Teller et al. |
| 7,277,741 B2 | 10/2007 | Debreczeny et al. |
| 7,284,904 B2 | 10/2007 | Tokita et al. |
| 7,285,090 B2 | 10/2007 | Stivoric et al. |
| 7,294,105 B1 | 11/2007 | Islam |
| 7,295,879 B2 | 11/2007 | Denker et al. |
| 7,297,119 B2 | 11/2007 | Westbrook et al. |
| 7,318,808 B2 | 1/2008 | Tarassenko et al. |
| 7,319,386 B2 | 1/2008 | Collins et al. |
| 7,336,187 B2 | 2/2008 | Hubbard, Jr. et al. |
| 7,346,380 B2 | 3/2008 | Axelgaard et al. |
| 7,382,247 B2 | 6/2008 | Welch et al. |
| 7,384,398 B2 | 6/2008 | Gagnadre et al. |
| 7,390,299 B2 | 6/2008 | Weiner et al. |
| 7,395,106 B2 | 7/2008 | Ryu et al. |
| 7,423,526 B2 | 9/2008 | Despotis |
| 7,423,537 B2 | 9/2008 | Bonnet et al. |
| 7,443,302 B2 | 10/2008 | Reeder et al. |
| 7,450,024 B2 | 11/2008 | Wildman et al. |
| 7,468,032 B2 | 12/2008 | Stahmann et al. |
| 8,116,841 B2 | 2/2012 | Bly et al. |
| 8,249,686 B2 | 8/2012 | Libbus et al. |
| 2001/0047127 A1 | 11/2001 | New, Jr. et al. |
| 2002/0019586 A1 | 2/2002 | Teller et al. |
| 2002/0019588 A1 | 2/2002 | Marro et al. |
| 2002/0028989 A1 | 3/2002 | Pelletier et al. |
| 2002/0032581 A1 | 3/2002 | Reitberg |
| 2002/0045836 A1 | 4/2002 | Alkawwas et al. |
| 2002/0088465 A1 | 7/2002 | Hill |
| 2002/0099277 A1 | 7/2002 | Harry et al. |
| 2002/0116009 A1 | 8/2002 | Fraser et al. |
| 2002/0123672 A1 | 9/2002 | Christophersom et al. |
| 2002/0123674 A1 | 9/2002 | Plicchi et al. |
| 2002/0138017 A1 | 9/2002 | Bui et al. |
| 2002/0167389 A1 | 11/2002 | Uchikoba et al. |
| 2003/0009092 A1 | 1/2003 | Parker |
| 2003/0023184 A1 | 1/2003 | Pitts-Crick et al. |
| 2003/0028221 A1 | 2/2003 | Zhu et al. |
| 2003/0028327 A1 | 2/2003 | Brunner et al. |
| 2003/0051144 A1 | 3/2003 | Williams |
| 2003/0055460 A1 | 3/2003 | Owens et al. |
| 2003/0083581 A1 | 5/2003 | Taha et al. |
| 2003/0085717 A1 | 5/2003 | Cooper |
| 2003/0087244 A1 | 5/2003 | McCarthy |
| 2003/0092975 A1 | 5/2003 | Casscells, III et al. |
| 2003/0093125 A1 | 5/2003 | Zhu et al. |
| 2003/0093298 A1 | 5/2003 | Hernandez et al. |
| 2003/0100367 A1 | 5/2003 | Cooke |
| 2003/0135127 A1 | 7/2003 | Sackner et al. |
| 2003/0143544 A1 | 7/2003 | McCarthy |
| 2003/0149349 A1 | 8/2003 | Jensen |
| 2003/0187370 A1 | 10/2003 | Kodama |
| 2003/0191503 A1 | 10/2003 | Zhu et al. |
| 2003/0212319 A1 | 11/2003 | Magill |
| 2003/0221687 A1 | 12/2003 | Kaigler |
| 2003/0233129 A1 | 12/2003 | Matos |
| 2004/0006279 A1 | 1/2004 | Arad (Abboud) |
| 2004/0010303 A1 | 1/2004 | Bolea et al. |
| 2004/0015058 A1 | 1/2004 | Besson et al. |
| 2004/0019292 A1 | 1/2004 | Drinan et al. |
| 2004/0044293 A1 | 3/2004 | Burton |
| 2004/0049132 A1 | 3/2004 | Barron et al. |
| 2004/0073094 A1 | 4/2004 | Baker |
| 2004/0073126 A1 | 4/2004 | Rowlandson |
| 2004/0077954 A1 | 4/2004 | Oakley et al. |
| 2004/0100376 A1 | 5/2004 | Lye et al. |
| 2004/0102683 A1 | 5/2004 | Khanuja et al. |
| 2004/0106951 A1 | 6/2004 | Edman et al. |
| 2004/0127790 A1 | 7/2004 | Lang et al. |
| 2004/0133079 A1 | 7/2004 | Mazar et al. |
| 2004/0133081 A1 | 7/2004 | Teller et al. |
| 2004/0134496 A1 | 7/2004 | Cho et al. |
| 2004/0143170 A1 | 7/2004 | DuRousseau |
| 2004/0147969 A1 | 7/2004 | Mann et al. |
| 2004/0152956 A1 | 8/2004 | Korman |
| 2004/0158132 A1 | 8/2004 | Zaleski |
| 2004/0167389 A1 | 8/2004 | Brabrand |
| 2004/0172080 A1 | 9/2004 | Stadler et al. |
| 2004/0199056 A1 | 10/2004 | Husemann et al. |
| 2004/0215240 A1 | 10/2004 | Lovett et al. |
| 2004/0215247 A1 | 10/2004 | Bolz |
| 2004/0220639 A1 | 11/2004 | Mulligan et al. |
| 2004/0225199 A1 | 11/2004 | Evanyk et al. |
| 2004/0225203 A1 | 11/2004 | Jemison et al. |
| 2004/0243018 A1 | 12/2004 | Organ et al. |
| 2004/0267142 A1 | 12/2004 | Paul |
| 2005/0004506 A1 | 1/2005 | Gyory |
| 2005/0015094 A1 | 1/2005 | Keller |
| 2005/0015095 A1 | 1/2005 | Keller |
| 2005/0020935 A1 | 1/2005 | Helzel et al. |
| 2005/0027175 A1 | 2/2005 | Yang |
| 2005/0027204 A1 | 2/2005 | Kligfield et al. |
| 2005/0027207 A1 | 2/2005 | Westbrook et al. |
| 2005/0027918 A1 | 2/2005 | Govindarajulu et al. |
| 2005/0043675 A1 | 2/2005 | Pastore et al. |
| 2005/0054944 A1 | 3/2005 | Nakada et al. |
| 2005/0059867 A1 | 3/2005 | Chung |
| 2005/0065445 A1 | 3/2005 | Arzbaecher et al. |
| 2005/0065571 A1 | 3/2005 | Imran |
| 2005/0070768 A1 | 3/2005 | Zhu et al. |

(56) References Cited

U.S. PATENT DOCUMENTS

| | | |
|---|---|---|
| 2005/0070778 A1 | 3/2005 | Lackey et al. |
| 2005/0080346 A1 | 4/2005 | Gianchandani et al. |
| 2005/0080460 A1 | 4/2005 | Wang et al. |
| 2005/0080463 A1 | 4/2005 | Stahmann et al. |
| 2005/0085734 A1 | 4/2005 | Tehrani |
| 2005/0091338 A1 | 4/2005 | de la Huerga |
| 2005/0096513 A1 | 5/2005 | Ozguz et al. |
| 2005/0113703 A1 | 5/2005 | Farringdon et al. |
| 2005/0124878 A1 | 6/2005 | Sharony |
| 2005/0124901 A1 | 6/2005 | Misczynski et al. |
| 2005/0124908 A1 | 6/2005 | Belalcazar et al. |
| 2005/0131288 A1 | 6/2005 | Turner et al. |
| 2005/0137464 A1 | 6/2005 | Bomba |
| 2005/0137626 A1 | 6/2005 | Pastore et al. |
| 2005/0148895 A1 | 7/2005 | Misczynski et al. |
| 2005/0158539 A1 | 7/2005 | Murphy et al. |
| 2005/0177038 A1 | 8/2005 | Kolpin et al. |
| 2005/0187482 A1 | 8/2005 | O'Brien et al. |
| 2005/0187796 A1 | 8/2005 | Rosenfeld et al. |
| 2005/0192488 A1 | 9/2005 | Bryenton et al. |
| 2005/0197654 A1 | 9/2005 | Edman et al. |
| 2005/0203433 A1 | 9/2005 | Singer |
| 2005/0203435 A1 | 9/2005 | Nakada |
| 2005/0203637 A1 | 9/2005 | Edman et al. |
| 2005/0206518 A1 | 9/2005 | Welch et al. |
| 2005/0215914 A1 | 9/2005 | Bornzin et al. |
| 2005/0215918 A1 | 9/2005 | Frantz et al. |
| 2005/0228234 A1 | 10/2005 | Yang |
| 2005/0228238 A1 | 10/2005 | Monitzer |
| 2005/0228244 A1 | 10/2005 | Banet |
| 2005/0239493 A1 | 10/2005 | Batkin et al. |
| 2005/0240087 A1 | 10/2005 | Keenan et al. |
| 2005/0251044 A1 | 11/2005 | Hoctor et al. |
| 2005/0256418 A1 | 11/2005 | Mietus et al. |
| 2005/0261598 A1 | 11/2005 | Banet et al. |
| 2005/0261743 A1 | 11/2005 | Kroll |
| 2005/0267376 A1 | 12/2005 | Marossero et al. |
| 2005/0267377 A1 | 12/2005 | Marossero et al. |
| 2005/0267381 A1 | 12/2005 | Benditt et al. |
| 2005/0267541 A1* | 12/2005 | Scheiner ............ A61N 1/36514 607/17 |
| 2005/0273023 A1 | 12/2005 | Bystrom et al. |
| 2005/0277841 A1 | 12/2005 | Shennib |
| 2005/0277842 A1 | 12/2005 | Silva |
| 2005/0277992 A1 | 12/2005 | Koh et al. |
| 2005/0280531 A1 | 12/2005 | Fadem et al. |
| 2005/0283197 A1 | 12/2005 | Daum et al. |
| 2005/0288601 A1 | 12/2005 | Wood et al. |
| 2006/0004300 A1 | 1/2006 | Kennedy |
| 2006/0004377 A1 | 1/2006 | Keller |
| 2006/0009697 A1 | 1/2006 | Banet et al. |
| 2006/0009701 A1 | 1/2006 | Nissila et al. |
| 2006/0010090 A1 | 1/2006 | Brockway et al. |
| 2006/0020218 A1 | 1/2006 | Freeman et al. |
| 2006/0025661 A1 | 2/2006 | Sweeney et al. |
| 2006/0030781 A1 | 2/2006 | Shennib |
| 2006/0030782 A1 | 2/2006 | Shennib |
| 2006/0030892 A1 | 2/2006 | Kadhiresan et al. |
| 2006/0031102 A1 | 2/2006 | Teller et al. |
| 2006/0041280 A1 | 2/2006 | Stahmann et al. |
| 2006/0047215 A1 | 3/2006 | Newman et al. |
| 2006/0052678 A1 | 3/2006 | Drinan et al. |
| 2006/0058543 A1 | 3/2006 | Walter et al. |
| 2006/0058593 A1 | 3/2006 | Drinan et al. |
| 2006/0064030 A1 | 3/2006 | Cosentino et al. |
| 2006/0064040 A1 | 3/2006 | Berger et al. |
| 2006/0064142 A1 | 3/2006 | Chavan et al. |
| 2006/0066449 A1 | 3/2006 | Johnson |
| 2006/0074283 A1 | 4/2006 | Henderson et al. |
| 2006/0074462 A1 | 4/2006 | Verhoef |
| 2006/0075257 A1 | 4/2006 | Martis et al. |
| 2006/0079793 A1* | 4/2006 | Mann ............... A61B 5/0215 600/486 |
| 2006/0084881 A1 | 4/2006 | Korzinov et al. |
| 2006/0085049 A1 | 4/2006 | Cory et al. |
| 2006/0089679 A1 | 4/2006 | Zhu et al. |
| 2006/0102476 A1 | 5/2006 | Niwa et al. |
| 2006/0116592 A1 | 6/2006 | Zhou et al. |
| 2006/0122474 A1 | 6/2006 | Teller et al. |
| 2006/0135858 A1 | 6/2006 | Nidd et al. |
| 2006/0142654 A1 | 6/2006 | Rytky |
| 2006/0142820 A1 | 6/2006 | Von Arx et al. |
| 2006/0149168 A1 | 7/2006 | Czarnek |
| 2006/0155183 A1 | 7/2006 | Kroecker et al. |
| 2006/0155200 A1 | 7/2006 | Ng |
| 2006/0161073 A1 | 7/2006 | Singer |
| 2006/0161205 A1 | 7/2006 | Mitrani et al. |
| 2006/0161459 A9 | 7/2006 | Rosenfeld et al. |
| 2006/0173257 A1 | 8/2006 | Nagai et al. |
| 2006/0173269 A1 | 8/2006 | Glossop |
| 2006/0195020 A1 | 8/2006 | Martin et al. |
| 2006/0195039 A1 | 8/2006 | Drew et al. |
| 2006/0195097 A1 | 8/2006 | Evans et al. |
| 2006/0195144 A1 | 8/2006 | Giftakis et al. |
| 2006/0202816 A1 | 9/2006 | Crump et al. |
| 2006/0212097 A1 | 9/2006 | Varadan et al. |
| 2006/0224051 A1 | 10/2006 | Teller et al. |
| 2006/0224072 A1 | 10/2006 | Shennib |
| 2006/0224079 A1 | 10/2006 | Washchuk |
| 2006/0235281 A1 | 10/2006 | Tuccillo |
| 2006/0235316 A1 | 10/2006 | Ungless et al. |
| 2006/0235489 A1 | 10/2006 | Drew et al. |
| 2006/0238333 A1 | 10/2006 | Welch et al. |
| 2006/0241641 A1 | 10/2006 | Albans et al. |
| 2006/0241701 A1 | 10/2006 | Markowitz et al. |
| 2006/0241722 A1 | 10/2006 | Thacker et al. |
| 2006/0247545 A1 | 11/2006 | St. Martin |
| 2006/0252999 A1 | 11/2006 | Devaul et al. |
| 2006/0253005 A1 | 11/2006 | Drinan et al. |
| 2006/0253044 A1 | 11/2006 | Zhang et al. |
| 2006/0258952 A1 | 11/2006 | Stahmann et al. |
| 2006/0264730 A1 | 11/2006 | Stivoric et al. |
| 2006/0264767 A1 | 11/2006 | Shennib |
| 2006/0264776 A1 | 11/2006 | Stahmann et al. |
| 2006/0271116 A1 | 11/2006 | Stahmann et al. |
| 2006/0276714 A1 | 12/2006 | Holt et al. |
| 2006/0281981 A1 | 12/2006 | Jang et al. |
| 2006/0281996 A1 | 12/2006 | Kuo et al. |
| 2006/0293571 A1 | 12/2006 | Bao et al. |
| 2006/0293609 A1 | 12/2006 | Stahmann et al. |
| 2007/0010721 A1 | 1/2007 | Chen et al. |
| 2007/0010750 A1 | 1/2007 | Ueno et al. |
| 2007/0015973 A1 | 1/2007 | Nanikashvili et al. |
| 2007/0015976 A1 | 1/2007 | Miesel et al. |
| 2007/0016089 A1 | 1/2007 | Fischell et al. |
| 2007/0021678 A1 | 1/2007 | Beck et al. |
| 2007/0021790 A1 | 1/2007 | Kieval et al. |
| 2007/0021792 A1 | 1/2007 | Kieval et al. |
| 2007/0021794 A1 | 1/2007 | Kieval et al. |
| 2007/0021796 A1 | 1/2007 | Kieval et al. |
| 2007/0021797 A1 | 1/2007 | Kieval et al. |
| 2007/0021798 A1 | 1/2007 | Kieval et al. |
| 2007/0021799 A1 | 1/2007 | Kieval et al. |
| 2007/0027388 A1 | 2/2007 | Chou |
| 2007/0027497 A1 | 2/2007 | Parnis |
| 2007/0032749 A1 | 2/2007 | Overall et al. |
| 2007/0038038 A1 | 2/2007 | Stivoric et al. |
| 2007/0038078 A1 | 2/2007 | Osadchy |
| 2007/0038255 A1 | 2/2007 | Kieval et al. |
| 2007/0038262 A1 | 2/2007 | Kieval et al. |
| 2007/0043301 A1 | 2/2007 | Martinsen et al. |
| 2007/0048224 A1 | 3/2007 | Howell et al. |
| 2007/0060800 A1 | 3/2007 | Drinan et al. |
| 2007/0060802 A1 | 3/2007 | Ghevondian et al. |
| 2007/0069887 A1 | 3/2007 | Welch et al. |
| 2007/0073132 A1 | 3/2007 | Vosch |
| 2007/0073168 A1 | 3/2007 | Zhang et al. |
| 2007/0073181 A1 | 3/2007 | Pu et al. |
| 2007/0073361 A1 | 3/2007 | Goren et al. |
| 2007/0082189 A1 | 4/2007 | Gillette |
| 2007/0083092 A1 | 4/2007 | Rippo et al. |
| 2007/0092862 A1 | 4/2007 | Gerber |
| 2007/0104840 A1 | 5/2007 | Singer |
| 2007/0106132 A1 | 5/2007 | Elhag et al. |

(56) References Cited

U.S. PATENT DOCUMENTS

| | | |
|---|---|---|
| 2007/0106137 A1 | 5/2007 | Baker, Jr. et al. |
| 2007/0106167 A1 | 5/2007 | Kinast |
| 2007/0118039 A1 | 5/2007 | Bodecker et al. |
| 2007/0123756 A1 | 5/2007 | Kitajima et al. |
| 2007/0123903 A1 | 5/2007 | Raymond et al. |
| 2007/0123904 A1 | 5/2007 | Stad et al. |
| 2007/0129622 A1 | 6/2007 | Bourget et al. |
| 2007/0129643 A1 | 6/2007 | Kwok et al. |
| 2007/0129769 A1 | 6/2007 | Bourget et al. |
| 2007/0142715 A1 | 6/2007 | Banet et al. |
| 2007/0142732 A1 | 6/2007 | Brockway et al. |
| 2007/0149282 A1 | 6/2007 | Lu et al. |
| 2007/0150008 A1 | 6/2007 | Jones et al. |
| 2007/0150009 A1 | 6/2007 | Kveen et al. |
| 2007/0150029 A1 | 6/2007 | Bourget et al. |
| 2007/0162089 A1 | 7/2007 | Mosesov |
| 2007/0167753 A1 | 7/2007 | Van Wyk et al. |
| 2007/0167848 A1 | 7/2007 | Kuo et al. |
| 2007/0167849 A1 | 7/2007 | Zhang et al. |
| 2007/0167850 A1 | 7/2007 | Russell et al. |
| 2007/0172424 A1 | 7/2007 | Roser |
| 2007/0173705 A1 | 7/2007 | Teller et al. |
| 2007/0180047 A1 | 8/2007 | Dong et al. |
| 2007/0180140 A1 | 8/2007 | Welch et al. |
| 2007/0191723 A1 | 8/2007 | Prystowsky et al. |
| 2007/0207858 A1 | 9/2007 | Breving |
| 2007/0208233 A1 | 9/2007 | Kovacs |
| 2007/0208235 A1 | 9/2007 | Besson et al. |
| 2007/0208262 A1 | 9/2007 | Kovacs |
| 2007/0208263 A1 | 9/2007 | John et al. |
| 2007/0232867 A1 | 10/2007 | Hansmann |
| 2007/0249946 A1 | 10/2007 | Kumar et al. |
| 2007/0250121 A1 | 10/2007 | Miesel et al. |
| 2007/0255120 A1 | 11/2007 | Rosnov |
| 2007/0255153 A1 | 11/2007 | Kumar et al. |
| 2007/0255184 A1 | 11/2007 | Shennib |
| 2007/0255531 A1 | 11/2007 | Drew |
| 2007/0260133 A1 | 11/2007 | Meyer |
| 2007/0260155 A1 | 11/2007 | Rapoport et al. |
| 2007/0260289 A1 | 11/2007 | Giftakis et al. |
| 2007/0273504 A1 | 11/2007 | Tran |
| 2007/0276273 A1 | 11/2007 | Watson, Jr |
| 2007/0282173 A1 | 12/2007 | Wang et al. |
| 2007/0299325 A1 | 12/2007 | Farrell et al. |
| 2008/0004499 A1 | 1/2008 | Davis |
| 2008/0004904 A1 | 1/2008 | Tran |
| 2008/0021336 A1 | 1/2008 | Dobak |
| 2008/0024293 A1 | 1/2008 | Stylos |
| 2008/0024294 A1 | 1/2008 | Mazar |
| 2008/0033260 A1 | 2/2008 | Sheppard et al. |
| 2008/0039700 A1 | 2/2008 | Drinan et al. |
| 2008/0058614 A1 | 3/2008 | Banet et al. |
| 2008/0058656 A1 | 3/2008 | Costello et al. |
| 2008/0059239 A1 | 3/2008 | Gerst et al. |
| 2008/0091089 A1 | 4/2008 | Guillory et al. |
| 2008/0114220 A1 | 5/2008 | Banet et al. |
| 2008/0139934 A1 | 6/2008 | McMorrow et al. |
| 2008/0146892 A1 | 6/2008 | LeBoeuf et al. |
| 2008/0167538 A1 | 7/2008 | Teller et al. |
| 2008/0171918 A1 | 7/2008 | Teller et al. |
| 2008/0171922 A1 | 7/2008 | Teller et al. |
| 2008/0171929 A1 | 7/2008 | Katims |
| 2008/0183052 A1 | 7/2008 | Teller et al. |
| 2008/0200774 A1 | 8/2008 | Luo |
| 2008/0214903 A1 | 9/2008 | Orbach |
| 2008/0220865 A1 | 9/2008 | Hsu |
| 2008/0221399 A1 | 9/2008 | Zhou et al. |
| 2008/0221402 A1 | 9/2008 | Despotis |
| 2008/0224852 A1 | 9/2008 | Dicks et al. |
| 2008/0228084 A1 | 9/2008 | Bedard et al. |
| 2008/0287751 A1 | 11/2008 | Stivoric et al. |
| 2008/0287752 A1 | 11/2008 | Stroetz et al. |
| 2008/0293491 A1 | 11/2008 | Wu et al. |
| 2008/0294019 A1 | 11/2008 | Tran |
| 2008/0294020 A1 | 11/2008 | Sapounas |
| 2008/0318681 A1 | 12/2008 | Rofougaran et al. |
| 2008/0319279 A1 | 12/2008 | Ramsay et al. |
| 2008/0319282 A1 | 12/2008 | Tran |
| 2008/0319290 A1 | 12/2008 | Mao et al. |
| 2009/0005016 A1 | 1/2009 | Eng et al. |
| 2009/0018410 A1 | 1/2009 | Coene et al. |
| 2009/0018456 A1 | 1/2009 | Hung |
| 2009/0048526 A1 | 2/2009 | Aarts et al. |
| 2009/0054737 A1 | 2/2009 | Magar et al. |
| 2009/0062670 A1 | 3/2009 | Sterling et al. |
| 2009/0073991 A1 | 3/2009 | Landrum et al. |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076344 A1 | 3/2009 | Libbus et al. |
| 2009/0076345 A1 | 3/2009 | Manicka et al. |
| 2009/0076346 A1 | 3/2009 | James et al. |
| 2009/0076348 A1 | 3/2009 | Manicka et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076401 A1 | 3/2009 | Mazar et al. |
| 2009/0076405 A1 | 3/2009 | Amurthur et al. |
| 2009/0076410 A1 | 3/2009 | Libbus et al. |
| 2009/0076559 A1 | 3/2009 | Libbus et al. |
| 2009/0182204 A1 | 7/2009 | Semler et al. |
| 2009/0234410 A1 | 9/2009 | Libbus et al. |
| 2009/0264792 A1 | 10/2009 | Mazar |
| 2009/0292194 A1 | 11/2009 | Libbus et al. |
| 2010/0056881 A1 | 3/2010 | Libbus et al. |
| 2010/0191310 A1 | 7/2010 | Bly et al. |
| 2011/0144470 A1 | 6/2011 | Mazar et al. |
| 2011/0245711 A1 | 10/2011 | Katra et al. |

\* cited by examiner

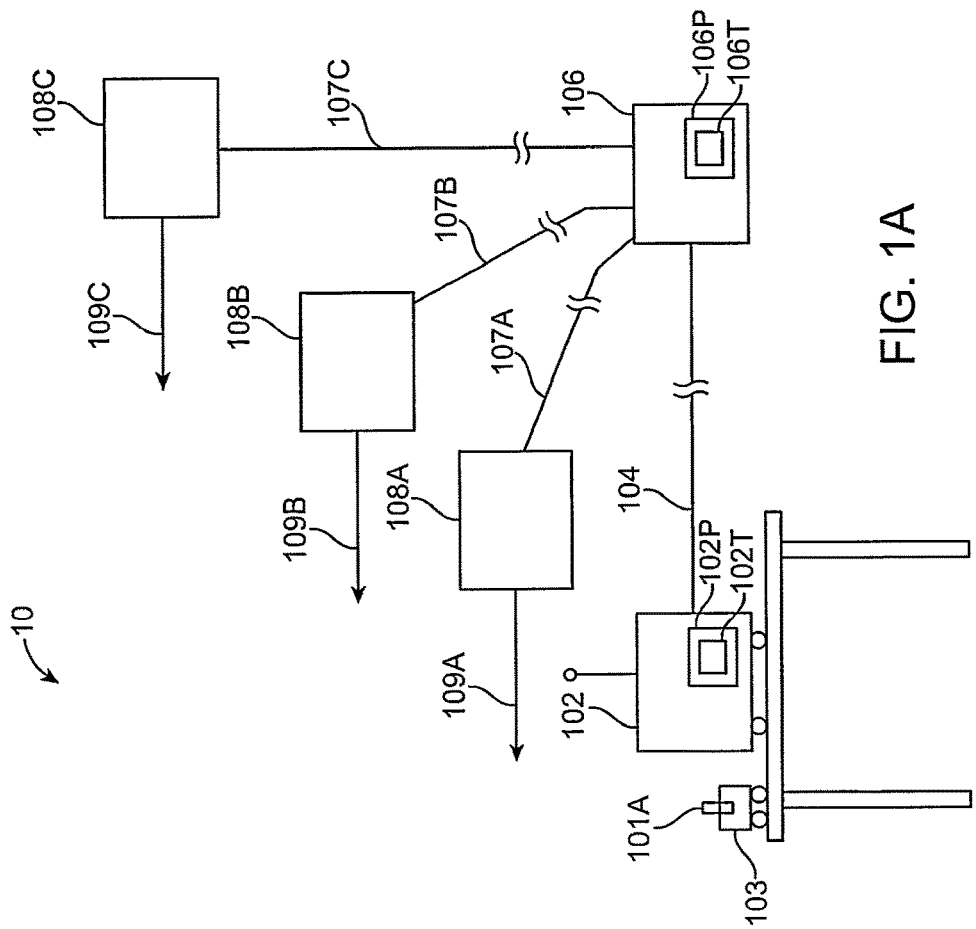
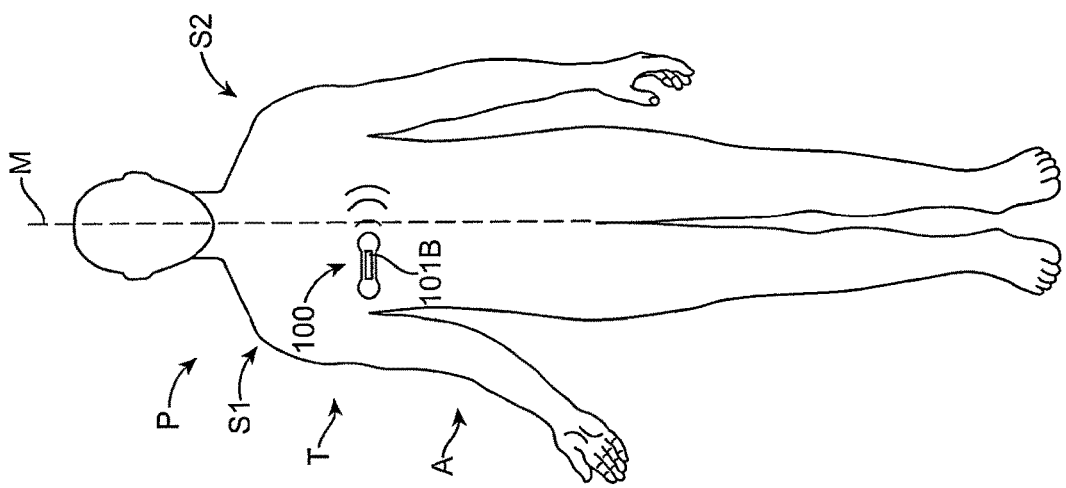
FIG. 1A

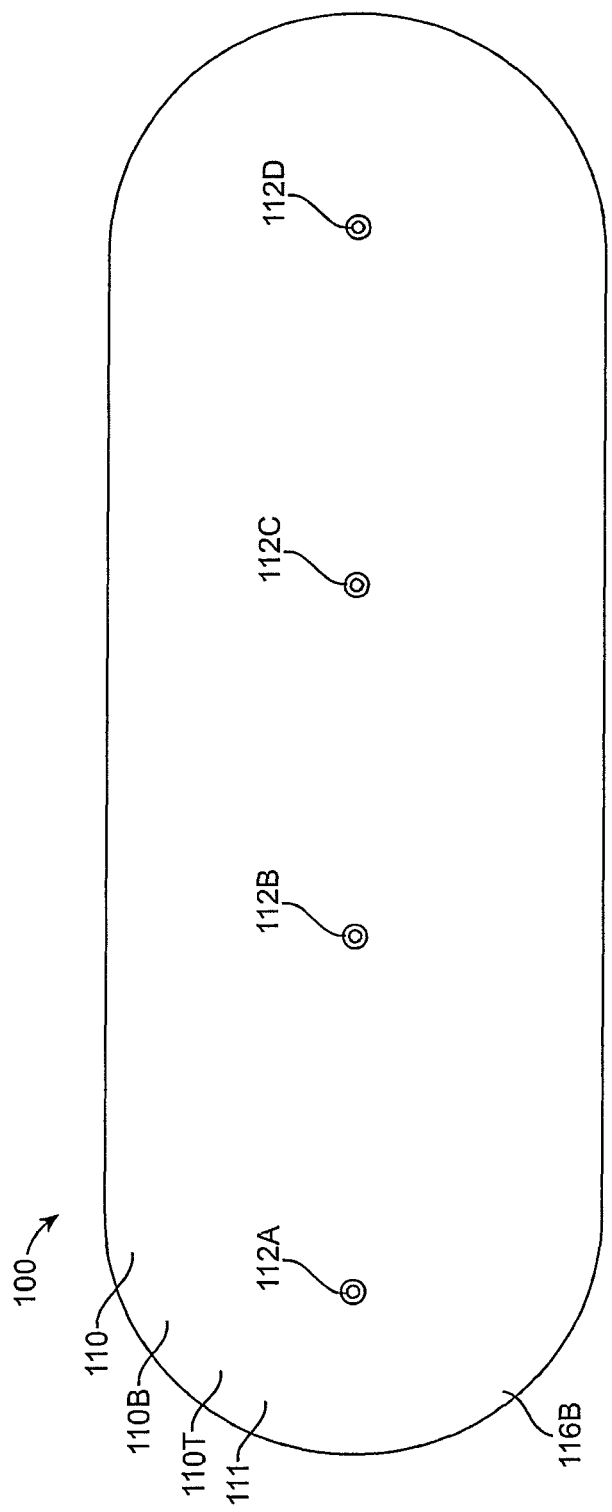

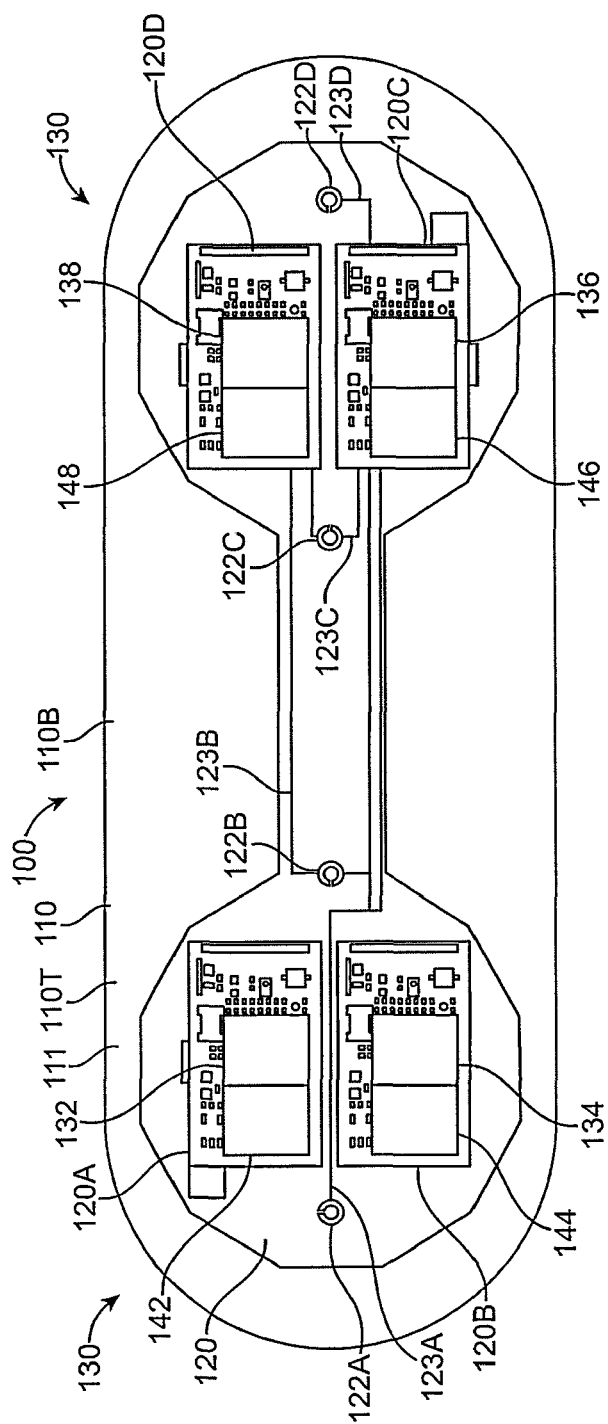
FIG. 1D
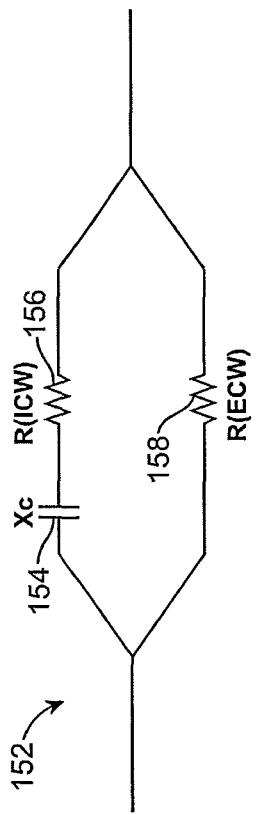
FIG. 1D1

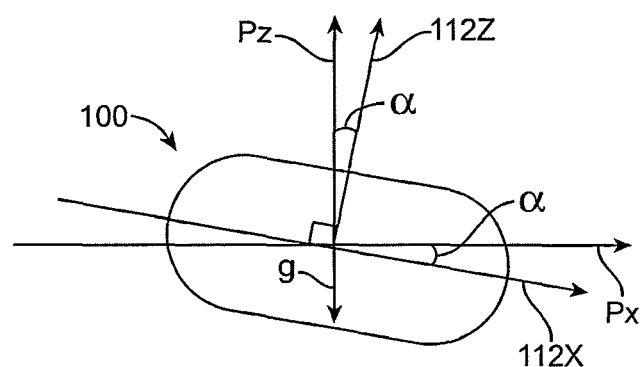
FIG. 1D2
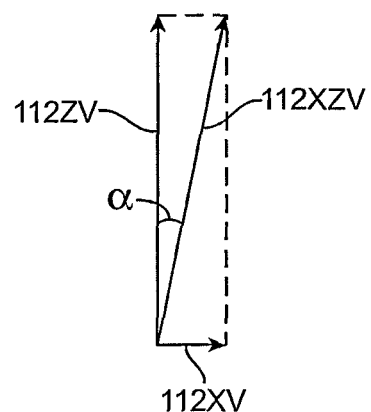
FIG. 1D3

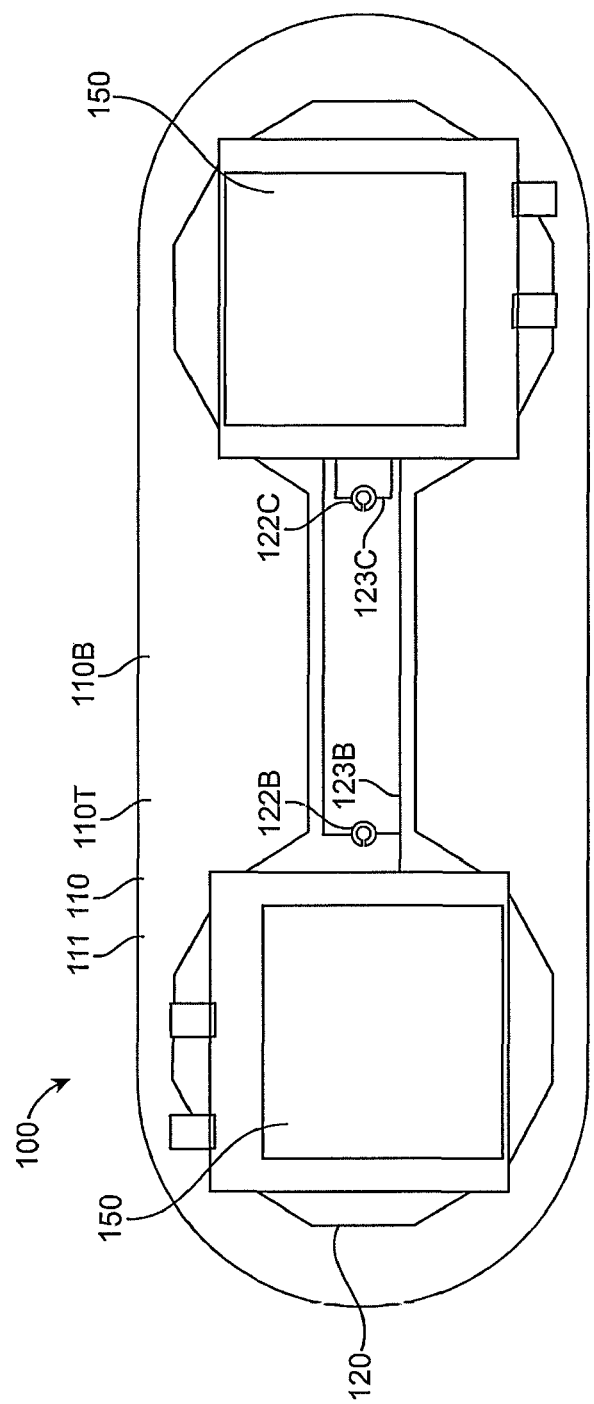

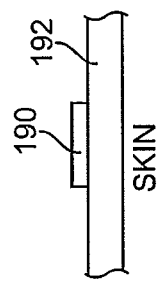
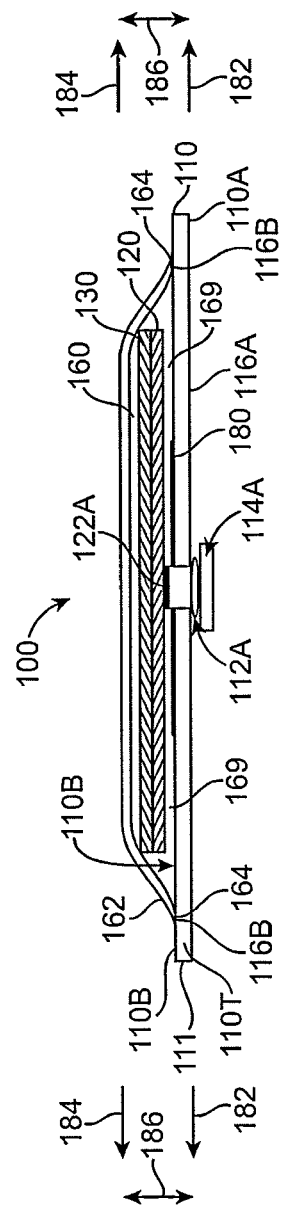

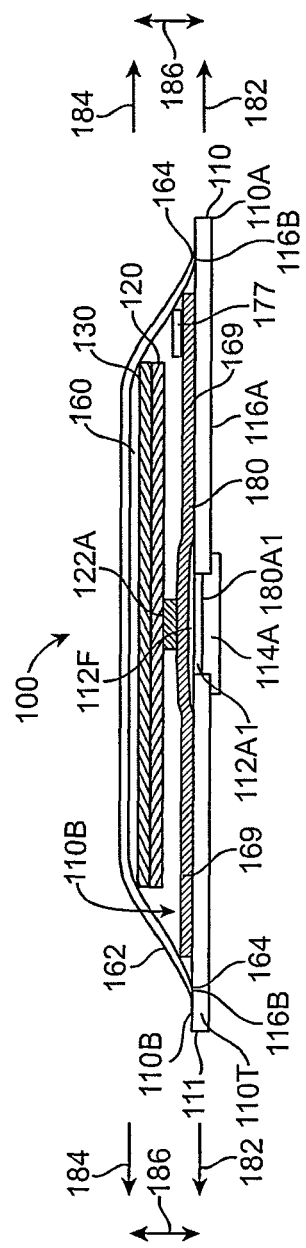
FIG. 1I1

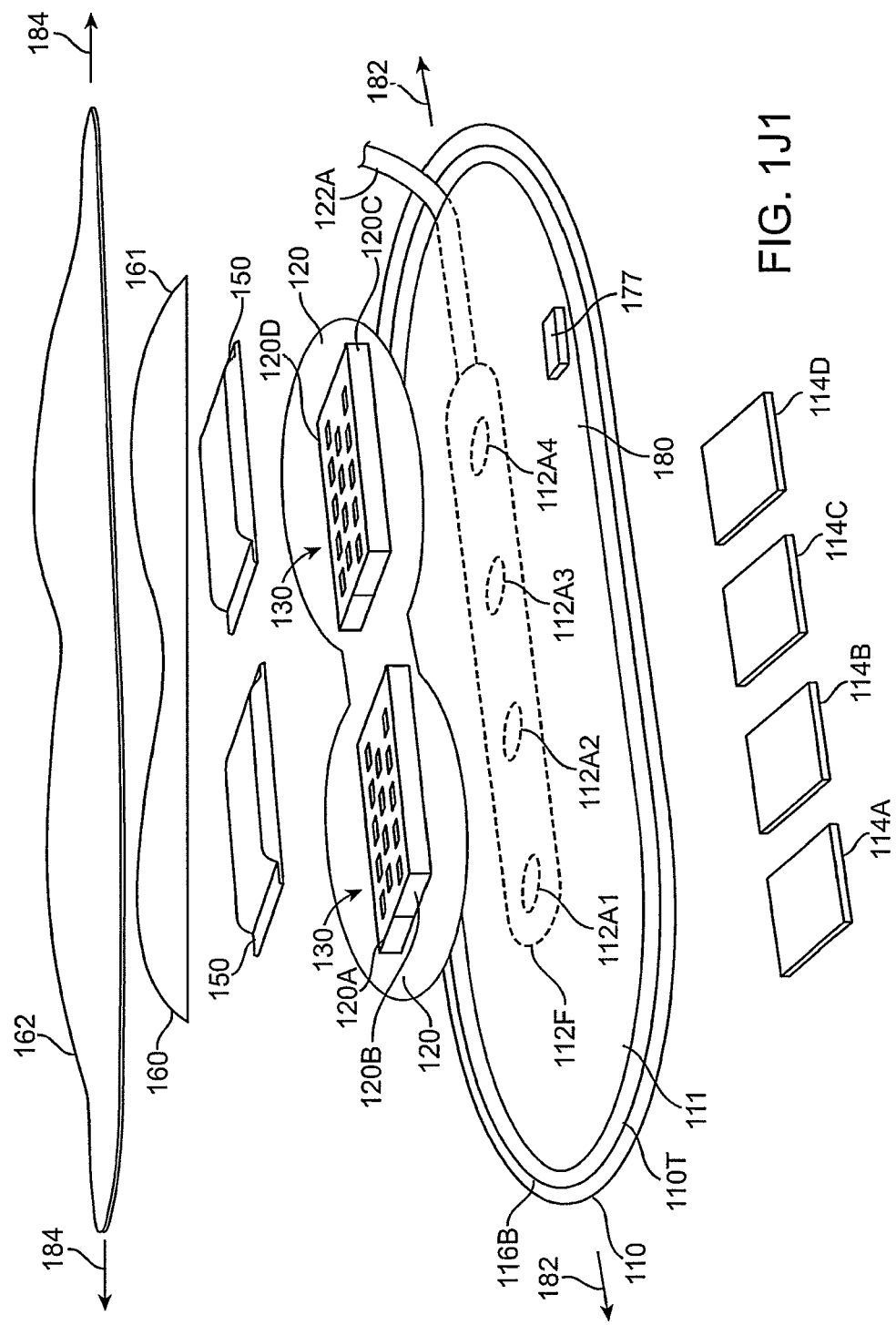
FIG. 1J1

200- Method of monitoring a patient
205- Adhere measurement device to patient to measure heart rate, activity, body posture, respiration rate and bioimpedance
210- Measure, store and process patient data with adherent device
212- Determine patient drug treatment
215- Transmit patient data from adherent device to gateway
220- Receive patient data with gateway
225- Measure, store and process patient data with gateway
230- Transmit patient data from gateway to remote server
235- Measure, store and process patient data with remote server
240- Identify CI with profile of remote heart rates
    241- determine profile of remote heart rates
    242- determine peak of profile of remote heart rates
    243- determine portion of profile above peak
    244- determine portion of profile below peak
    245- compare portion above peak to portion below peak
    246- identify CI when portion above peak is less than portion below
250- Identify CI with resting remote HR
    251- determine occurrence of heart rates corresponding to profile
    252- determine peak of the remote heart rates 254- determine remote resting HR based on peak of remote HR
    255- determine age corrected maximum HR
    256- determine HRR based on age corrected maximum HR and remote resting HR
    257- identify CI when HRR below threshold
260- Identify CI with maximum HR
    261- determine threshold activity amount based on patient data from a plurality of other patients
    262- determine patient activity above threshold
    263- determine heart rates corresponding to patient activity above threshold
    264- determine correlation of HR above threshold with one or more of activity, body posture, respiration rate and bioimpedance
    265- determine patient drug treatment and compliance
    266- determine CI based on patient drug treatment and correlation of HR above threshold with the one or more of one or more of activity, body posture, respiration rate and bioimpedance
270- Transmit notification to one or more of physician or patient based on identification of CI

Figure 2

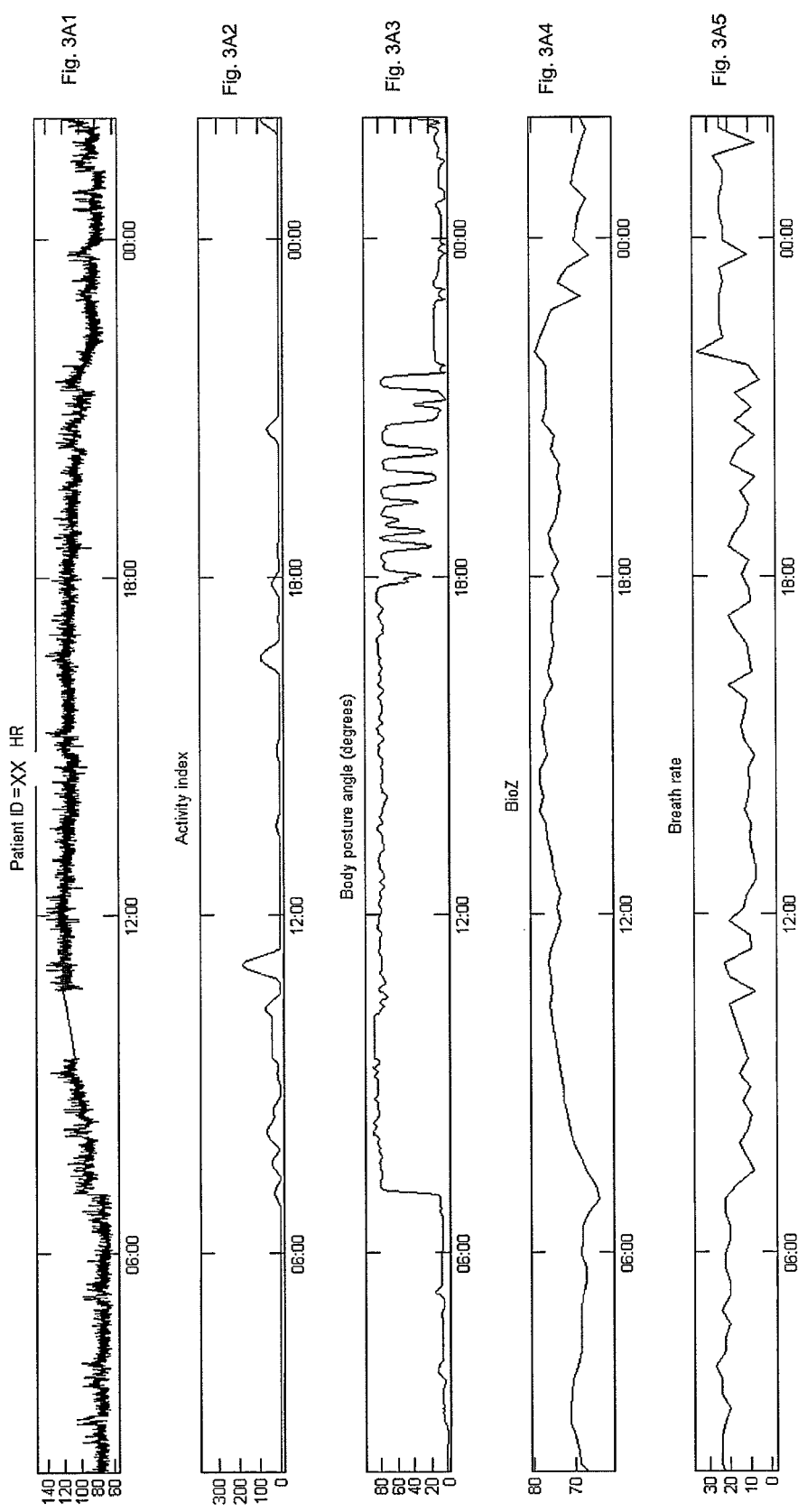

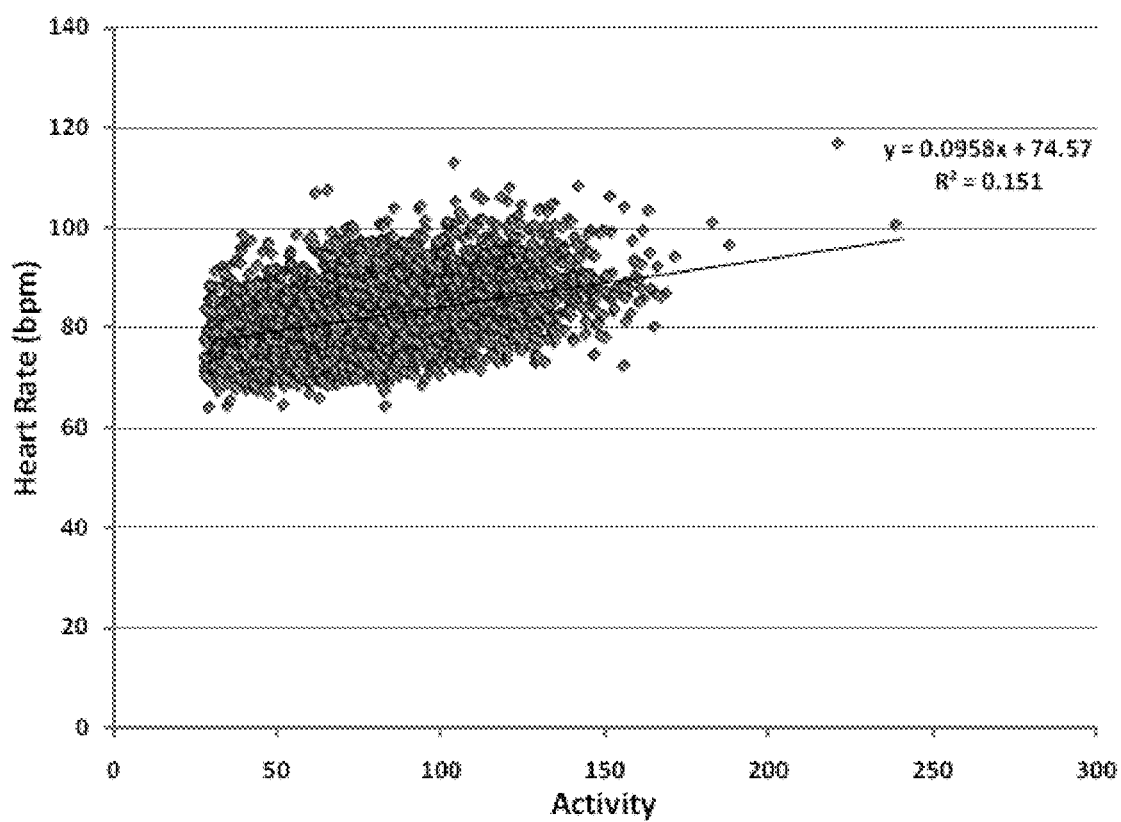
FIGURE 3D1

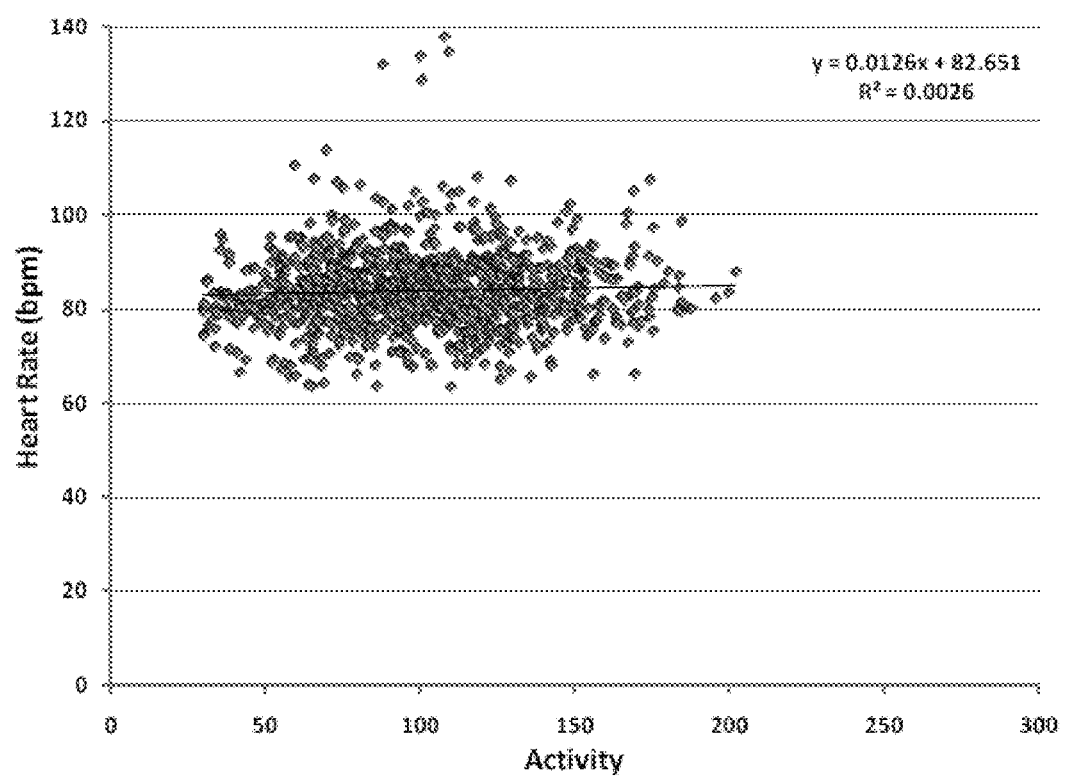
FIGURE 3D2

METHOD AND APPARATUS FOR REMOTE DETECTION AND MONITORING OF FUNCTIONAL CHRONOTROPIC INCOMPETENCE

CROSS-REFERENCES TO RELATED APPLICATIONS

This application is a continuation of U.S. patent application Ser. No. 12/910,076 filed Oct. 22, 2010 and titled "Method and Apparatus for Remote Detection and Monitoring of Functional Chronotropic Incompetence", which claims the benefit under 35 USC 119(e) of U.S. Provisional Application No. 61/253,866, filed on Oct. 22, 2009 and titled "Method and Apparatus for Remote Detection and Monitoring of Functional Chronotropic Incompetence", the entire disclosures of which are hereby incorporated by reference herein for all purposes.

BACKGROUND OF THE INVENTION

Patients are often treated for diseases and/or conditions associated with a compromised status of the patient, for example a compromised physiologic status. In some instances, a patient may report symptoms that require diagnosis to determine the underlying cause. For example, a patient may report fainting or dizziness that requires diagnosis, in which long term monitoring of the patient can provide useful information as to the physiologic status of the patient. In some instances a patient may have suffered a heart attack and require care and/or monitoring after release from the hospital.

Chronotropic incompetence (hereinafter "CI") can be a debilitating condition associated with high mortality and morbidity. Chronotropic incompetence can be defined as the inability for a patient to elevate heart rate to 85% of the age-predicted maximum heart rate (hereinafter "APMHR") level during exercise in a clinical environment. The determination of the ability of the patient to raise HR can be done by subjecting a patient to exercise in a clinic to elevate the patient HR, for example with a treadmill in a clinic.

Work in relation to embodiments of the present invention suggests that known methods and apparatus for determining CI may be less than ideal. At least some of the known methods and apparatus test the patient in a clinical setting and may not determine the presence of CI when the patient is located remote from the clinic, for example located at home. Although successful in determining the presence of CI in a clinical setting, current methods that rely on a controlled environment such as a treadmill in a clinic may not be well suited to determine CI when the patient is located remote from the clinic. For example, in at least some instances the patient may be somewhat frail and not well suited to exercise on his or her own. Also, current methods of determining the maximum HR of the patient assume that the patient is able to exercise the level of his or her capacity when the maximum HR is measured, and in at least some instances such an assumption may not be appropriate, such as for patients with respiratory and cardiac diseases, as well as patients with physical disability.

Another approach to determining cardiac function related to CI in a patient can be to determine the heart rate reserve (hereinafter "HRR") of the patient, in which the HRR is determined with the resting HR of the patient. However, in at least some instances it can be difficult to determine the resting HR of the patient in the clinic. In at least some instances, measurements of a patient in a clinic can be nervous and the heart rate can be elevated, for example with white coat syndrome, and the patient may receive an incorrect diagnosis in at least some instances. Further, at least some of the present methods of measuring HR remotely may not provide appropriate data to determine the resting HR when the patient is located remote from the clinic.

Therefore, a need exists for improved patient monitoring. Ideally, such improved patient monitoring would avoid at least some of the short-comings of the present methods and devices.

BRIEF SUMMARY OF THE INVENTION

Embodiments of the present invention provide methods and apparatus to determine the presence of and track functional CI in an in-home setting under conditions of daily living. The remote monitoring of the patient can determine the presence of functional CI and identify functional CI so as to allow appropriate intervention and treatment. The functional CI of the patient can be determined safely and in many ways with the patient located outside the clinic. For example, the functional CI of the patient may be determined with one or more of a profile of measured patient heart rates, a measured maximum patient heart rate, or a peak of the heart rate profile, such as the peak of a heart rate distribution profile. The functional CI of the patient may be determined with the measured heart rate profile, in which the measured heart rate profile may correspond to heart rates substantially less than the maximum heart rate of the patient, such that the heart rate can be safely measured when the patient is remote from a health care provider. Alternatively or in combination, the functional CI of the patient may be determined based on a peak of the remotely measured heart rate profile. Further, the functional CI may be determined based on statistical measurements of the heart rate profile such as a location, for example central tendency, and variability, for example dispersion, of the measured heart rate. For example, the relative amounts of the profile of heart rates above the peak and heart rates below the peak can be compared to determine the functional CI. The peak of the heart rate profile of the remote heart rate data may be used to determine the heart rate reserve and functional CI of the patient.

The measured distribution of heart rates of the remotely measured patient heart rate data can be combined with one or more of the measured activity data, measured respiration data, the measured orientation and the measured impedance data so as to determine the functional CI of the patient. The measured activity data of the patient can be combined with the heart rate data to determine a measured maximum heart rate of the patient when the patient exercises. For example, the peak activity of the patient can be determined and compared to a threshold value, and the maximum heart rate of the patient may correspond to the activity of the patient above the threshold. Alternatively or in combination, the maximum heart rate of the patient may comprise an estimated maximum heart rate of the patient, and the presence of functional CI determined based on the estimated maximum heart rate and the age predicted maximum heart rate, such that the functional CI may be determined without requiring elevation of the heart rate of the patient.

The measured patient data can come from one or more of many sources of data such as an adherent device, or an implantable device, or combinations thereof. An implantable device can be used to measure heart rate data. Alternatively or in combination an adherent device can be used to measure heart rate data. Additional data can be measured, for example accelerometer data from an adherent device.

In a first aspect, embodiments provide an apparatus to monitor a patient. A processor system comprises at least one processor having a tangible medium with instructions of a computer program embodied thereon, the processor system configured to receive heart rate data of the patient and determine a profile of the heart rates and wherein the processor is configured to identify chronotropic incompetence of the patient based on the profile of the heart rates.

In many embodiments, the computer program comprises instructions to identify the functional CI with one or more measurement of location of the heart rate data, measures of dispersion and variability of the heart rate data, skewness and kurtosis of the heart rate data, or comparison of portions around a mode of a single modal mounded distribution.

In many embodiments, the computer program comprises instructions to determine a peak of the profile and a first portion of the profile and a second portion of the profile, the first portion corresponding to a first amount of occurrences of first heart rates less than the peak and the second portion corresponding to a second amount of occurrences of second heart rates greater than the peak and wherein the chronotropic incompetence is identified based on the second amount smaller than the first amount.

In another aspect, embodiments provide an apparatus to monitor a remote patient, the apparatus comprises a processor system comprising at least one processor having a tangible medium with instructions of a computer program embodied thereon. The processor system is configured to receive heart rate data of the remote patient and determine a distribution of the heart rates, and the processor is configured to identify a chronotropic incompetence of the patient based on the distribution of heart rates.

In many embodiments, the computer program comprises instructions to receive respiration data of the patient and activity data of the patient and instructions to combine the heart rate data with the respiration data and activity data to identify the chronotropic incompetence.

In many embodiments, the computer program comprises instructions to determine a peak of the distribution and a first portion of the distribution and a second portion of the distribution, the first portion corresponding to a first amount of occurrences of first heart rates less than the peak and the second portion of the distribution corresponding to a second amount of occurrences of second heart rates greater than the peak. The chronotropic incompetence is identified based on the second amount smaller than the first amount.

In another aspect, embodiments provide a method of monitoring a patient. A processor system is provided which comprises at least one processor having a tangible medium with instructions of a computer program embodied thereon, the processor system configured to receive heart rate data of the patient and determine a profile of the heart rates. The chronotropic incompetence of the patient is identified based on the profile of the heart rates.

In another aspect, embodiments provide an apparatus to monitor a remote patient. A processor system comprises at least one processor having a tangible medium with instructions of a computer program embodied thereon, the processor system configured to receive data of the remote patient comprising heart rate data of the patient and activity data of the patient. The processor system comprises instructions to determine activity of the patient to a threshold activity amount, and the processor system comprises instructions to identify a chronotropic incompetence of the patient based on the heart rate data corresponding to activity of the patient above the threshold.

In many embodiments, the processor system comprises instructions to determine a maximum heart rate of the heart rate data corresponding to the activity of the patient above the threshold.

In many embodiments, the processor system comprises instructions to determine a correlation of the maximum heart rate with one or more of the patient activity, patient body posture, patient breath rate or patient respiration rate and wherein the processor system is configured to identify CI based on the correlation.

In many embodiments, the data of the patient comprises drug data of the patient and wherein the processor system comprises instructions to identify CI based on the drug data and the correlation.

In many embodiments, the patient data comprises data from an adherent device measured remotely and wherein the processor system comprises instructions to determine the threshold amount from a plurality of remote patients and corresponds to a percentile of patient activity of the plurality of remote patients.

In another aspect, embodiments provide a method of monitoring a remote patient. A processor system is provided that comprises at least one processor having a tangible medium with instructions of a computer program embodied thereon, and the processor system is configured to receive data of the remote patient comprising heart rate data of the patient and activity data of the patient. The processor system comprises instructions to determine activity of the patient to a threshold activity amount. A chronotropic incompetence of the patient is identified based on the heart rate data corresponding to activity of the patient above the threshold.

In another aspect, embodiments provide an apparatus to monitor a remote patient. A processor system comprises at least one processor having a tangible medium with instructions of a computer program embodied thereon, and the processor system comprises instructions to receive heart rate data of the remote patient and to determine a peak of heart rates of the remote patient. The processor system comprises instructions to identify a chronotropic incompetence of the patient based on the peak.

In many embodiments, the heart rates comprise a profile of heart rates, and the peak comprises a peak of the profile.

In many embodiments, the heart rates comprise a distribution of heart rates, and the peak comprises a mode of the distribution.

In many embodiments, the processor system comprises instructions to determine a heart rate reserve based on a difference of a maximum age predicted maximum heart rate and the peak, and the processor system is configured to determine the CI based on the heart rate reserve determined with the peak.

In another aspect, embodiments provide a method of monitoring a remote patient. A processor system is provided that comprises at least one processor having a tangible medium with instructions of a computer program embodied thereon, and the processor system comprises instructions to receive heart rate data of the remote patient and to determine a peak of heart rates of the remote patient. A chronotropic incompetence of the patient is identified based on the peak.

In another aspect, embodiments provide an apparatus to monitor a patient having a skin. An adherent device to measure patient data comprises wireless communication circuitry and measurement circuitry, the measurement circuitry is coupled to at least two electrodes, a respiration sensor and an activity sensor. The adherent device comprising a support with an adhesive to adhere the at least two electrodes to the skin and support the wireless communication circuitry, the processor circuitry and the measurement circuitry with the skin. A server is located remote from the patient to receive the patient data. A gateway is coupled to each of the adherent device and the server with wireless communication to transmit the patient data. One or more of the adherent device, the server or the gateway comprises at least one processor having a tangible memory medium with instructions of a computer program embodied thereon to determine a chronotropic incompetence of the patient based on the patient data measured with the at least two electrodes, the respiration sensor and the activity sensor.

In many embodiments, the at least one processor comprises instructions to determine a distribution of heart rates of the patient and wherein the at least one processor is configured to determine the chronotropic incompetence based on the distribution heart rates.

In many embodiments, the distribution of heart rates of the patient corresponds to a plurality of heart levels and an occurrence of each level.

In many embodiments, the computer program comprises instructions to determine a peak of the distribution and a first portion of the distribution and a second portion of the distribution, the first portion corresponding to a first amount of occurrences of first heart rates less than the peak and the second portion of the distribution corresponding to a second amount of occurrences of second heart rates greater than the peak and wherein the chronotropic incompetence is determined based on the second amount smaller than the first amount.

In many embodiments, the at least one processor comprises instructions to fit the distribution to a Gaussian distribution and determine a skew of the distribution and wherein the chronotropic incompetence is determined based on the skew.

In many embodiments, the at least one processor comprises instructions to determine a distribution of heart rates of the patient, the distribution corresponding heart rates less than a maximum heart rate of the patient and wherein the at least one processor is configured to determine the chronotropic incompetence based on the distribution heart rate intervals corresponding to less than the maximum heart rate of the patient.

In many embodiments, the at least one processor comprises instructions to determine a distribution of heart rates of the patient, the distribution corresponding to heart rates less than a maximum heart rate of the patient and wherein the at least one processor comprises instructions to determine the maximum heart rate of the patient based on the distribution heart rate intervals corresponding to less than the maximum heart rate of the patient.

In many embodiments, the at least one processor comprises instructions to determine the chronotropic incompetence of the patient based on the maximum heart rate of the patient.

In many embodiments, the at least one processor comprises instructions to determine the maximum heart rate of the patient based on the distribution of heart rates corresponding to less than the maximum heart rate of the patient.

In another aspect, embodiments provide a method of monitoring a patient. Heart rate data of the patient is measured. A processor system is provided which comprises at least one processor having a tangible medium with instructions of a computer program embodied thereon. The processor system receives heart rate data of the patient and determines a distribution of the heart rates, and the processor determines a chronotropic incompetence of the patient based on the distribution of heart rates.

In many embodiments, the heart rate data comprise data measured from a patch adhered to the patient for at least about one week, and the heart rate data is transmitted with wireless communication.

In another aspect, embodiments provide an apparatus to monitor a patient. The apparatus comprises an adherent device means for measuring patient data, and a processor means for determining a chronotropic incompetence of the patient. The adherent device means may comprise the adherent device as described herein and the processor means for determining the chronotropic incompetence of the patient may comprise the computer readable instructions embedded on one or more processor as described herein.

BRIEF DESCRIPTION OF THE DRAWINGS

FIG. 1A shows a patient and a monitoring system comprising an adherent device, according to embodiments of the present invention;

FIG. 1C shows a top view of the adherent patch, as in FIG. 1B;

FIG. 1D shows a printed circuit board and electronic components over the adherent patch, as in FIG. 1C;

FIG. 1D1 shows an equivalent circuit that can be used to determine optimal frequencies for determining patient hydration, according to embodiments of the present invention;

FIG. 1D2 shows adherent devices as in FIGS. 1A-1D positioned on a patient to determine orientation of the adherent patch on the patient, according to embodiments of the present invention;

FIG. 1D3 shows vectors from a 3D accelerometer to determine orientation of the measurement axis of the patch adhered on the patient, according to embodiments of the present invention;

FIG. 1E shows batteries positioned over the printed circuit board and electronic components as in FIG. 1D;

FIGS. 1I and 1J show a side cross-sectional view and an exploded view, respectively, of the adherent device as in FIGS. 1A to 1H;

FIGS. 1I1 and 1J1 show a side cross-sectional view and an exploded view, respectively, of embodiments of the adherent device with a temperature sensor affixed to the gel cover;

FIG. 1K shows at least one electrode configured to electrically couple to a skin of the patient through a breathable tape, according to embodiments of the present invention;

FIG. 2 shows a method of monitoring a person, in accordance with embodiments of the present invention;

FIGS. 3A1 to 3A5 show heart rate, activity index, body posture, impedance, and respiration rate measured from an adherent device adhered to the skin of the patient;

FIG. 3D1 shows correlation of heart rate with activity for patients without functional CI; and FIG. 3D2 shows correlation of heart rate with activity for patients with functional CI.

DETAILED DESCRIPTION OF THE INVENTION

Figure 1B:
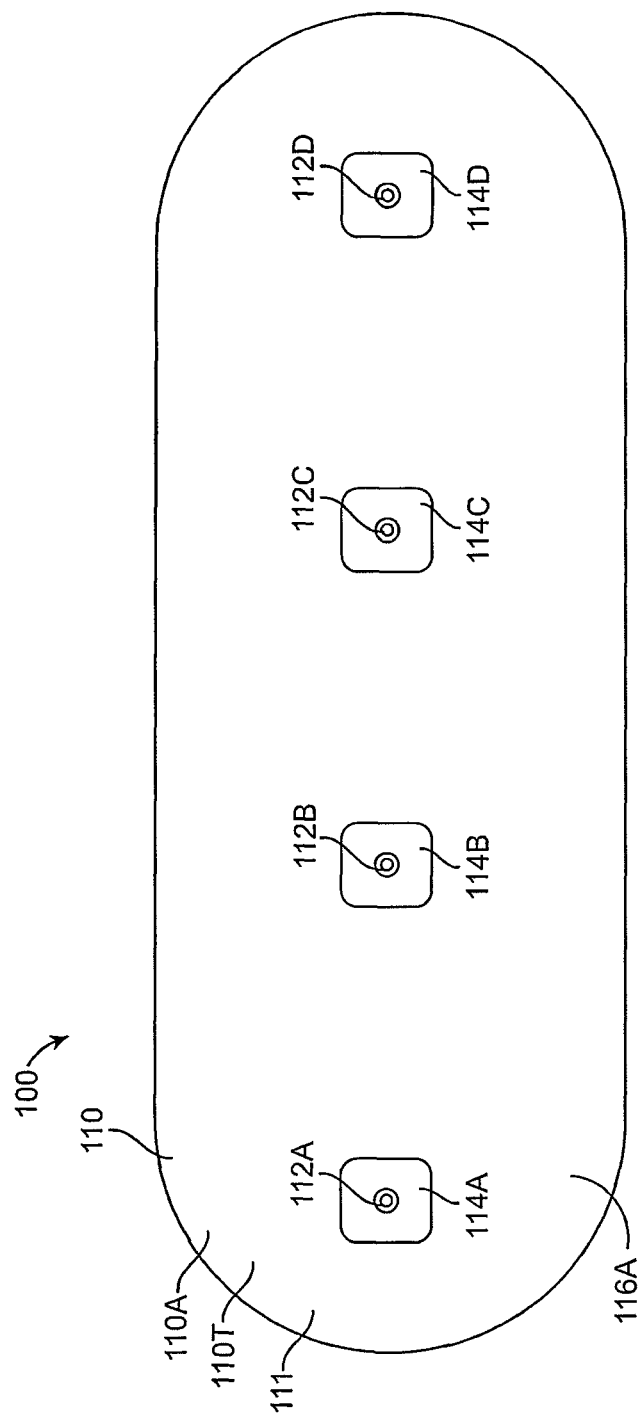
FIG. 1B shows a bottom view of the adherent device as in FIG. 1A comprising an adherent patch.

Embodiments comprise an adherent wireless communication apparatus and methods to measure patient data and determine the presence of functional chronotropic incompetence (CI). The patient measurement device may comprise one or more of an adherent device or an implantable device, and processor system can determine CI with heart rate and activity data collected from the patient under conditions of daily living, for example when the patient is home.

As used herein, chronotropic incompetence encompasses a failure of the heart rate to elevate sufficiently when the patient is active. For example, although CI may comprise a failure of the heart rate to elevate to a percentage amount of 85% of the age predicted maximum heart rate during exercise, this amount can change based on pharmacological modification of heart rate response. Therefore, the determination of the CI of the patient can change based on treatment of the patient with pharmacologic compositions, and the determination of the CI of the patient can be based on patient treatment with medication in additional to measure physiological patient data as described herein.

As used herein functional CI encompasses a CI condition where the patient's heart rate fails to accommodate the patient's activities of daily living, resulting in debilitation under sub-maximum activity levels and heart rates.

The adherent device and processor system are capable of monitoring and tracking patient activity and heart rate (hereinafter "HR") so as to assess CI in a natural living environment outside the clinic, such as at home. The adherent device can also measure and compute respiratory rate and patient activity, such that correspondence among CI, respiration and activity can be determined. For example one or more processors may comprise instructions of a computer program so as to correlate the impact of CI to changes in other physiological parameters and patient symptoms. This combination of patient data can improve determination of the CI and correlate the CI to patient symptoms. For example the level of debilitation that CI is causing can be correlated to patient symptoms.

The adherent device and processor system can measure patient heart rate data and determine a maximum heart rate of the patient that can be used to monitor the patient. For example, the maximum heart rate of the patient may be determined without a cardiac stress test, and with patient heart rate data that is less than the actual maximum heart rate of the patient, such that the maximum heart rate can be determined safely when the patient is remote from a clinic. For example, an estimated maximum heart rate of the patient can be determined based on a patient a histogram distribution of the heart rate. Alternatively or in combination, the measured heart rate data can be adjusted based on one or more of patient activity and patient respiration.

The determined maximum heart rate of the patient can be combined in many ways with patient data to monitor the patient and trigger alerts when the patient is at risk, for example. The adherent device and processor system can determine the age predicted maximum heart rate, the age predicted heart rate reserve, the percent heart rate reserve. For example the adherent device and processor system can be configured to determine the age predicted maximum heart rate (APMHR) based on the patient age (hereinafter "AGE") with the formula:

APMHR=220−AGE.

The APMHR can be combined with the determined maximum heart rate of the patient to determine the CI of the patient. For example, the ratio of the maximum heart rate to the APMHR and corresponding percentage can be determined. When the maximum HR of the patient corresponds to less than about 85% of the APMHR, the patient be identified as having CI.

The adherent device and processor system can determine the age predicted heart rate reserve (hereinafter "APHRR") with the formula APHRR=APMHR−resting HR.

The adherent device and processor system can determine the percent heart rate reserve (hereinafter "% HRR") with the formula % HRR=[(maximum HR)−(Resting HR)]*100/ APHRR.

The adherent device and processor system can determine histograms for each of the HR, the RR interval and the activity, and determine the correlation between these measurement data and derive indices from each of these measurement data.

In the many embodiments, the adherent device can communicate wirelessly so as to transmit the multi-sensor data to a server located remote from the patient. The adherent device can communicate to the server with a wireless communication gateway. The wireless communication gateway can receive data from the adherent device with wireless communication, for example Bluetooth™, and the gateway can transmit the data to the server with wireless communication, for example a cellular communication protocol.

The remote server may comprise a computer program having instructions embodied in a tangible memory medium so as to instruct the processor to combine the collected data from the device as well as demographic and medication information resident on the server, in order to determine the presence of patient CI. The instructions of the program can also calculate the CI parameters and raise an alert if a adverse condition is detected. Alternatively or in combination, the gateway near the patient may comprise a processor having a tangible memory medium, and the gateway may comprise instructions of a computer program embodied on the tangible medium, so as to instruct the gateway processor to combine the collected data from the adherent device as well as the demographic and the medication information.

In many embodiments, the adherent device may comprise a processor and perform real-time diagnostic assessment of CI and alert the patient and/or care provider via audio and/or visual cues based on standard CI classification cut-off levels. This is possible with an adherent device that can store the theoretical age predicted maximum heart rate (hereinafter "APMHR") and then track patient activity and heart rate so as to assess CI in real time. Alternatively or in combination, the adherent device can retrieve patient data related to the APMHR from the server, for example the patient's age when the patient has used the adherent device before and the patient data is stored on a database of the server. This retrieval of the APMHR data can improve the accuracy of the device as used and prevent errors, as the patient age, for example, can be stored in the data base such that the physician or patient from entering the age manually and may also avoid data entry errors.

Alternatively or in combination, the adherent device may store the CI assessment data for future offline data download, or transmit the data in real-time directly or indirectly (through an intermediary device that is paired to the adherent device) to a data storage entity.

The systems, methods and apparatus as described herein may comprise instructions of a processor system so as to determine functional CI based on an analysis of the envelop of HR histogram profile and the profile of HR change with activity so as to assess cardio-acceleration and cardio-blunting.

There may be additional embodiments and implementations for this method and apparatus based on the teachings described herein that will be apparent to a person of ordinary skill in the art.

FIG. 1A shows a patient P and a monitoring system 10. Patient P comprises a midline M, a first side S1, for example a right side, and a second side S2, for example a left side. Monitoring system 10 comprises an adherent device 100. Adherent device 100 can be adhered to a patient P at many locations, for example thorax T of patient P. In many embodiments, the adherent device may adhere to one side of the patient, from which side data can be collected. Work in relation with embodiments of the present invention suggests that location on a side of the patient can provide comfort for the patient while the device is adhered to the patient. The monitoring system 10 and adherent device 100 may comprise components as described in U.S. Pub. No. US-2009-0076345-A1, entitled "Adherent Device with Multiple Physiological Sensors", the full disclosure of which is incorporated herein by reference and suitable for combination in accordance with some embodiments of the present invention as described herein.

Monitoring system 10 includes components to transmit data to a remote center 106. Remote center 106 can be located in a different building from the patient, for example in the same town as the patient, and can be located as far from the patient as a separate continent from the patient, for example the patient located on a first continent and the remote center located on a second continent. Adherent device 100 can communicate wirelessly to an intermediate device 102, for example with a single wireless hop from the adherent device on the patient to the intermediate device. Intermediate device 102 can communicate with remote center 106 in many ways, for example with an Internet connection and/or with a cellular connection. In many embodiments, monitoring system 10 comprises a distributed processor system with at least one processor comprising a tangible medium of device 100, at least one processor 102P of intermediate device 102, and at least one processor 106P at remote center 106, each of which processors can be in electronic communication with the other processors. At least one processor 102P comprises a tangible medium 102T, and at least one processor 106P comprises a tangible medium 106T. Remote processor 106P may comprise a backend server located at the remote center. Remote center 106 can be in communication with a health care provider 108A with a communication system 107A, such as the Internet, an intranet, phone lines, wireless and/or satellite phone. Health care provider 108A, for example a family member, can be in communication with patient P with a communication, for example with a two way communication system, as indicated by arrow 109A, for example by cell phone, email, or landline. Remote center 106 can be in communication with a health care professional, for example a physician 108B, with a communication system 107B, such as the Internet, an intranet, phone lines, wireless and/or satellite phone. Physician 108B can be in communication with patient P with a communication, for example with a two way communication system, as indicated by arrow 109B, for example by cell phone, email, landline. Remote center 106 can be in communication with an emergency responder 108C, for example a 911 operator and/or paramedic, with a communication system 107C, such as the Internet, an intranet, phone lines, wireless and/or satellite phone. Emergency responder 108C can travel to the patient as indicated by arrow 109C. Thus, in many embodiments, monitoring system 10 comprises a closed loop system in which patient care can be monitored and implemented from the remote center in response to signals from the adherent device.

In many embodiments, the adherent device may continuously monitor physiological parameters, communicate wirelessly with a remote center, and provide alerts when necessary. The system may comprise an adherent patch, which attaches to the patient's thorax and contains sensing electrodes, battery, memory, logic, and wireless communication capabilities. In some embodiments, the patch can communicate with the remote center, via the intermediate device in the patient's home. In some embodiments, remote center 106 receives the patient data and applies a patient evaluation algorithm, for example the prediction algorithm to predict patient physiological or mental deterioration. In some embodiments, the algorithm may comprise an algorithm to predict impending patient physiological or mental deterioration, for example based on decreased hydration and activity. When a flag is raised, the center may communicate with the patient, hospital, nurse, and/or physician to allow for therapeutic intervention, for example to prevent further physiological or mental deterioration.

The adherent device may be affixed and/or adhered to the body in many ways. For example, with at least one of the following an adhesive tape, a constant-force spring, suspenders around shoulders, a screw-in microneedle electrode, a pre-shaped electronics module to shape fabric to a thorax, a pinch onto roll of skin, or transcutaneous anchoring. Patch and/or device replacement may occur with a keyed patch (e.g. two-part patch), an outline or anatomical mark, a low-adhesive guide (place guide|remove old patch|place new patch|remove guide), or a keyed attachment for chatter reduction. The patch and/or device may comprise an adhesiveless embodiment (e.g. chest strap), and/or a low-irritation adhesive for sensitive skin. The adherent patch and/or device can comprise many shapes, for example at least one of a dogbone, an hourglass, an oblong, a circular or an oval shape.

In many embodiments, the adherent device may comprise a reusable electronics module with replaceable patches, and each of the replaceable patches may include a battery. The module may collect cumulative data for approximately 90 days and/or the entire adherent component (electronics+patch) may be disposable. In a completely disposable embodiment, a "baton" mechanism may be used for data transfer and retention, for example baton transfer may include baseline information. In some embodiments, the device may have a rechargeable module, and may use dual battery and/or electronics modules, wherein one module 101A can be recharged using a charging station 103 while the other module 101B is placed on the adherent patch with connectors. In some embodiments, the intermediate device 102 may comprise the charging module, data transfer, storage and/or transmission, such that one of the electronics modules can be placed in the intermediate device for charging and/or data transfer while the other electronics module is worn by the patient.

System 10 can perform the following functions: initiation, programming, measuring, storing, analyzing, communicating, predicting, and displaying. The adherent device may contain a subset of the following physiological sensors: bioimpedance, respiration, respiration rate variability, heart rate (ave, min, max), heart rhythm, heart rate variability (HRV), heart rate turbulence (HRT), heart sounds (e.g. S3), respiratory sounds, blood pressure, activity, posture, wake/sleep, orthopnea, temperature/heat flux, and weight. The activity sensor may comprise one or more of the following: ball switch, accelerometer, minute ventilation, HR, bioimpedance noise, skin temperature/heat flux, BP, muscle noise, posture.

The adherent device can wirelessly communicate with remote center 106. The communication may occur directly (via a cellular or Wi-Fi network), or indirectly through intermediate device 102. Intermediate device 102 may consist of multiple devices, which can communicate wired or wirelessly to relay data to remote center 106.

In many embodiments, instructions are transmitted from remote site 106 to a processor supported with the adherent patch on the patient, and the processor supported with the patient can receive updated instructions for the patient treatment and/or monitoring, for example while worn by the patient.

FIG. 1B shows a bottom view of adherent device 100 as in FIG. 1A comprising an adherent patch 110. Adherent patch 110 comprises a first side, or a lower side 110A, that is oriented toward the skin of the patient when placed on the patient. In many embodiments, adherent patch 110 comprises a tape 110T which is a material, preferably breathable, with an adhesive 116A. Patient side 110A comprises adhesive 116A to adhere the patch 110 and adherent device 100 to patient P. Electrodes 112A, 112B, 112C and 112D are affixed to adherent patch 110. In many embodiments, at least four electrodes are attached to the patch, for example six electrodes. In some embodiments the patch comprises two electrodes, for example two electrodes to measure the electrocardiogram (ECG) of the patient. Gel 114A, gel 114B, gel 114C and gel 114D can each be positioned over electrodes 112A, 112B, 112C and 112D, respectively, to provide electrical conductivity between the electrodes and the skin of the patient. In many embodiments, the electrodes can be affixed to the patch 110, for example with known methods and structures such as rivets, adhesive, stitches, etc. In many embodiments, patch 110 comprises a breathable material to permit air and/or vapor to flow to and from the surface of the skin.

FIG. 1C shows a top view of the adherent patch 100, as in FIG. 1B. Adherent patch 100 comprises a second side, or upper side 110B. In many embodiments, electrodes 112A, 112B, 112C and 112D extend from lower side 110A through adherent patch 110 to upper side 110B. An adhesive 116B can be applied to upper side 110B to adhere structures, for example a breathable cover, to the patch such that the patch can support the electronics and other structures when the patch is adhered to the patient. The PCB may comprise completely flex PCB, rigid PCB, rigid PCB combined flex PCB and/or rigid PCB boards connected by cable.

FIG. 1D shows a printed circuit boards and electronic components over adherent patch 110, as in FIGS. 1A to 1C. In some embodiments, a printed circuit board (PCB), for example flex printed circuit board 120, may be connected to electrodes 112A, 112B, 112C and 112D with connectors 122A, 122B, 122C and 122D. Flex printed circuit board 120 can include traces 123A, 123B, 123C and 123D that extend to connectors 122A, 122B, 122C and 122D, respectively, on the flex PCB. Connectors 122A, 122B, 122C and 122D can be positioned on flex printed circuit board 120 in alignment with electrodes 112A, 112B, 112C and 112D so as to electrically couple the flex PCB with the electrodes. In some embodiments, connectors 122A, 122B, 122C and 122D may comprise insulated wires and/or a film with conductive ink that provide strain relief between the PCB and the electrodes. For example, connectors 122A, 122B, 122C and 122D may comprise a flexible film, such as at least one of known polyester film or known polyurethane file coated with a conductive ink, for example a conductive silver ink. Examples of structures to provide strain relief are also described in U.S. patent application Ser. No. 12/209,288, entitled "Adherent Device with Multiple Physiological Sensors", filed on Sep. 12, 2008. In some embodiments, additional PCB's, for example rigid PCB's 120A, 120B, 120C and 120D, can be connected to flex printed circuit board 120. Electronic components 130 can be connected to flex printed circuit board 120 and/or mounted thereon. In some embodiments, electronic components 130 can be mounted on the additional PCB's.

Electronic components 130 comprise components to take physiologic measurements, transmit data to remote center 106 and receive commands from remote center 106. In many embodiments, electronics components 130 may comprise known low power circuitry, for example complementary metal oxide semiconductor (CMOS) circuitry components. Electronics components 130 comprise an activity sensor and activity circuitry 134, impedance circuitry 136 and electrocardiogram circuitry, for example ECG circuitry 136. In some embodiments, electronics circuitry 130 may comprise a microphone and microphone circuitry 142 to detect an audio signal from within the patient, and the audio signal may comprise a heart sound and/or a respiratory sound, for example an S3 heart sound and a respiratory sound with rales and/or crackles.

Electronics circuitry 130 may comprise a temperature sensor, for example a thermistor in contact with the skin of the patient, and temperature sensor circuitry 144 to measure a temperature of the patient, for example a temperature of the skin of the patient. A temperature sensor may be used to determine the sleep and wake state of the patient. The temperature of the patient can decrease as the patient goes to sleep and increase when the patient wakes up.

Work in relation to embodiments of the present invention suggests that skin temperature may effect impedance and/or hydration measurements, and that skin temperature measurements may be used to correct impedance and/or hydration measurements. In some embodiments, increase in skin temperature or heat flux can be associated with increased vasodilation near the skin surface, such that measured impedance measurement decreased, even through the hydration of the patient in deeper tissues under the skin remains substantially unchanged. Thus, use of the temperature sensor can allow for correction of the hydration signals to more accurately assess the hydration, for example extra cellular hydration, of deeper tissues of the patient, for example deeper tissues in the thorax.

Electronics circuitry 130 may comprise a processor 146. Processor 146 comprises a tangible medium, for example read only memory (ROM), electrically erasable programmable read only memory (EEPROM) and/or random access memory (RAM). Electronic circuitry 130 may comprise real time clock and frequency generator circuitry 148. In some embodiments, processor 136 may comprise the frequency generator and real time clock. The processor can be configured to control a collection and transmission of data from the impedance circuitry electrocardiogram circuitry and the accelerometer. In many embodiments, device 100 comprises a distributed processor system, for example with multiple processors on device 100.

In many embodiments, electronics components 130 comprise wireless communications circuitry 132 to communicate with remote center 106. Printed circuit board 120 may comprise an antenna to facilitate wireless communication. The antenna may be integral with printed circuit board 120 or may be separately coupled thereto. The wireless communication circuitry can be coupled to the impedance circuitry, the electrocardiogram circuitry and the accelerometer to transmit to a remote center with a communication protocol at least one of the hydration signal, the electrocardiogram signal or the inclination signal. In specific embodiments, wireless communication circuitry is configured to transmit the hydration signal, the electrocardiogram signal and the inclination signal to the remote center with a single wireless hop, for example from wireless communication circuitry 132 to intermediate device 102. The communication protocol comprises at least one of Bluetooth, ZigBee, WiFi, WiMAX, IR, amplitude modulation or frequency modulation. In many embodiments, the communications protocol comprises a two way protocol such that the remote center is capable of issuing commands to control data collection.

Intermediate device 102 may comprise a data collection system to collect and store data from the wireless transmitter. The data collection system can be configured to communicate periodically with the remote center. The data collection system can transmit data in response to commands from remote center 106 and/or in response to commands from the adherent device.

Activity sensor and activity circuitry 134 can comprise many known activity sensors and circuitry. In many embodiments, the accelerometer comprises at least one of a piezoelectric accelerometer, capacitive accelerometer or electromechanical accelerometer. The accelerometer may comprises a 3-axis accelerometer to measure at least one of an inclination, a position, an orientation or acceleration of the patient in three dimensions. Work in relation to embodiments of the present invention suggests that three dimensional orientation of the patient and associated positions, for example sitting, standing, lying down, can be very useful when combined with data from other sensors, for example ECG data and/or hydration data.

Impedance circuitry 136 can generate both hydration data and respiration data. In many embodiments, impedance circuitry 136 is electrically connected to electrodes 112A, 112B, 112C and 112D in a four pole configuration, such that electrodes 112A and 112D comprise outer electrodes that are driven with a current and comprise force electrodes that force the current through the tissue. The current delivered between electrodes 112A and 112D generates a measurable voltage between electrodes 112B and 112C, such that electrodes 112B and 112C comprise inner, sense, electrodes that sense and/or measure the voltage in response to the current from the force electrodes. In some embodiments, electrodes 112B and 112C may comprise force electrodes and electrodes 112A and 112D may comprise sense electrodes. The voltage measured by the sense electrodes can be used to measure the impedance of the patient and determine the respiration rate and/or hydration of the patient. The electrocardiogram circuitry may be coupled to the sense electrodes to measure the electrocardiogram signal, for example as described in U.S. patent application Ser. No. 12/209,288, entitled "Adherent Device with Multiple Physiological Sensors", filed on Sep. 12, 2008.

FIG. 1D1 shows an equivalent circuit 152 that can be used to determine optimal frequencies for measuring patient hydration. Work in relation to embodiments of the present invention indicates that the frequency of the current and/or voltage at the force electrodes can be selected so as to provide impedance signals related to the extracellular and/or intracellular hydration of the patient tissue. Equivalent circuit 152 comprises an intracellular resistance 156, or R(ICW) in series with a capacitor 154, and an extracellular resistance 158, or R(ECW). Extracellular resistance 158 is in parallel with intracellular resistance 156 and capacitor 154 related to capacitance of cell membranes. In many embodiments, impedances can be measured and provide useful information over a wide range of frequencies, for example from about 0.5 kHz to about 200 KHz. Work in relation to embodiments of the present invention suggests that extracellular resistance 158 can be significantly related extracellular fluid and to patient physiological or mental physiological or mental deterioration, and that extracellular resistance 158 and extracellular fluid can be effectively measured with frequencies in a range from about 0.5 kHz to about 20 kHz, for example from about 1 kHz to about 10 kHz. In some embodiments, a single frequency can be used to determine the extracellular resistance and/or fluid. As sample frequencies increase from about 10 kHz to about 20 kHz, capacitance related to cell membranes decrease the impedance, such that the intracellular fluid contributes to the impedance and/or hydration measurements. Thus, many embodiments of the present invention measure hydration with frequencies from about 0.5 kHz to about 20 kHz to determine patient hydration.

In many embodiments, impedance circuitry 136 can be configured to determine respiration of the patient. In specific embodiments, the impedance circuitry can measure the hydration at 25 Hz intervals, for example at 25 Hz intervals using impedance measurements with a frequency from about 0.5 kHz to about 20 kHz.

ECG circuitry 138 can generate electrocardiogram signals and data from two or more of electrodes 112A, 112B, 112C and 112D in many ways. In some embodiments, ECG circuitry 138 is connected to inner electrodes 112B and 122C, which may comprise sense electrodes of the impedance circuitry as described above. In some embodiments, ECG circuitry 138 can be connected to electrodes 112A and 112D so as to increase spacing of the electrodes. The inner electrodes may be positioned near the outer electrodes to increase the voltage of the ECG signal measured by ECG circuitry 138. In many embodiments, the ECG circuitry may measure the ECG signal from electrodes 112A and 112D when current is not passed through electrodes 112A and 112D, for example with switches as described in U.S. App. No. 60/972,527, the full disclosure of which has been previously incorporated herein by reference.

FIG. 1D2 shows an adherent device, for example adherent device 100, positioned on patient P to determine orientation of the adherent patch. X-axis 112X of device 100 is inclined at an angle α to horizontal axis Px of patient P. Z-axis 112Z of device 100 is inclined at angle α to vertical axis Pz of patient P. Y-axis 112Y may be inclined at a second angle, for example α, to anterior posterior axis Py and vertical axis Pz. As the accelerometer of adherent device 100 can be sensitive to gravity, inclination of the patch relative to axis of the patient can be measured, for example when the patient stands.

ECG circuitry 138 can be coupled to the electrodes in many ways to define an electrocardiogram vector. For example electrode 112A can be coupled to a positive amplifier terminal of ECG circuitry 138 and electrode 112D can be coupled to a negative amplifier terminal of ECG circuitry 138 to define an orientation of an electrocardiogram vector along the electrode measurement axis. To define an electrocardiogram vector with an opposite orientation electrode 112D can be couple to the positive amplifier terminal of ECG circuitry 138 and electrode 112A can be coupled to the negative amplifier terminal of ECG circuitry 138. The ECG circuitry may be coupled to the inner electrodes so as to define an ECG vector along a measurement axis of the inner electrodes.

FIG. 1D3 shows vectors from a 3D accelerometer to determine orientation of the measurement axis of the patch adhered on the patient. The orientation can be determined for each patch adhered to the patient. A Z-axis vector 112ZV can be measured along vertical axis 112Z with an accelerometer signal from axis 134Z of accelerometer 134A. An X-axis vector 112XV can be measured along horizontal axis 112X with an accelerometer signal from axis 134X of accelerometer 134A. Inclination angle α can be determined in response to X-axis vector 112XV and Z-axis vector 112ZV, for example with vector addition of X-axis vector 112XV and Z-axis vector 112ZV. An inclination angle α for the patch along the Y and Z axes can be similarly obtained an accelerometer signal from axis 134Y of accelerometer 134A and vector 112ZV.

FIG. 1E shows batteries 150 positioned over the flex printed circuit board and electronic components as in FIG. 1D. Batteries 150 may comprise rechargeable batteries that can be removed and/or recharged. In some embodiments, batteries 150 can be removed from the adherent patch and recharged and/or replaced.

Figure 1F:
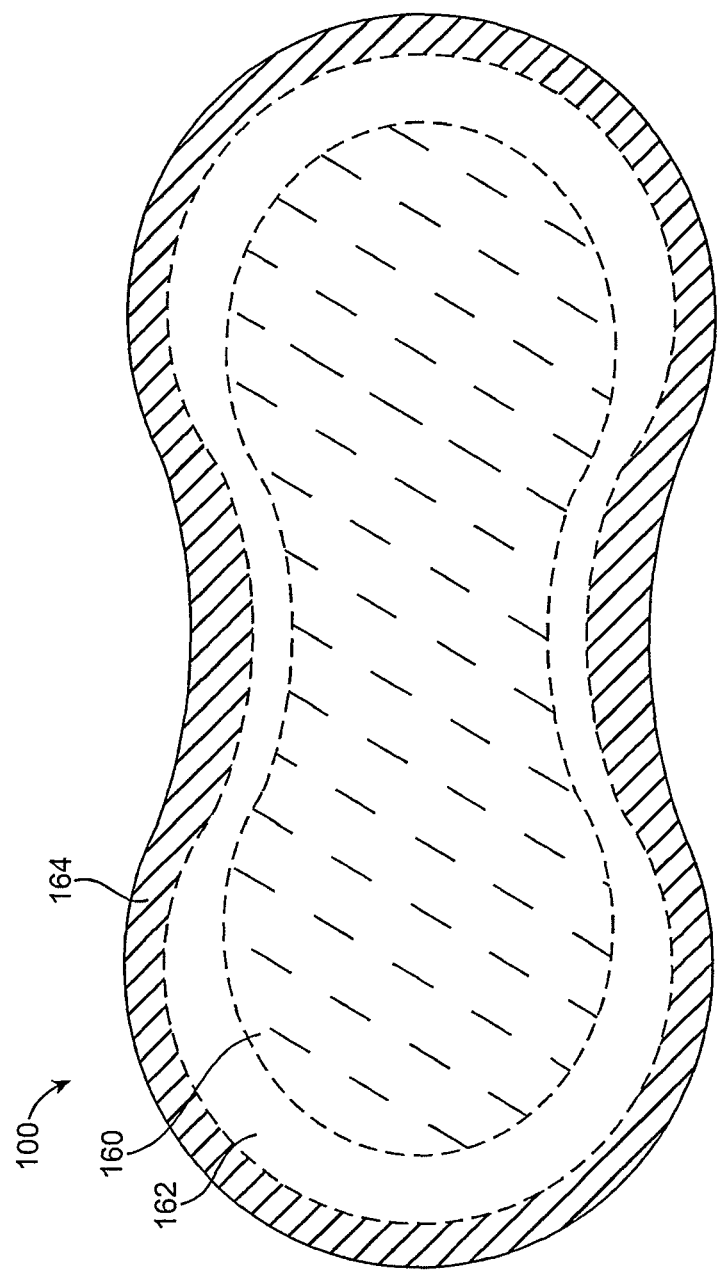
FIG. 1F shows a top view of an electronics housing and a breathable cover over the batteries, electronic components and printed circuit board as in FIG. 1E.

FIG. 1F shows a top view of a cover 162 over the batteries, electronic components and flex printed circuit board as in FIGS. 1A to 1E. In many embodiments, an electronics housing 160 may be disposed under cover 162 to protect the electronic components, and in some embodiments electronics housing 160 may comprise an encapsulant over the electronic components and PCB. In some embodiments, cover 162 can be adhered to adherent patch 110 with an adhesive 164 on an underside of cover 162. In many embodiments, electronics housing 160 may comprise a water proof material, for example a sealant adhesive such as epoxy or silicone coated over the electronics components and/or PCB. In some embodiments, electronics housing 160 may comprise metal and/or plastic. Metal or plastic may be potted with a material such as epoxy or silicone.

Cover 162 may comprise many known biocompatible cover, casing and/or housing materials, such as elastomers, for example silicone. The elastomer may be fenestrated to improve breathability. In some embodiments, cover 162 may comprise many known breathable materials, for example polyester, polyamide, nylon and/or elastane (Spandex™). The breathable fabric may be coated to make it water resistant, waterproof, and/or to aid in wicking moisture away from the patch.

Figure 1H:
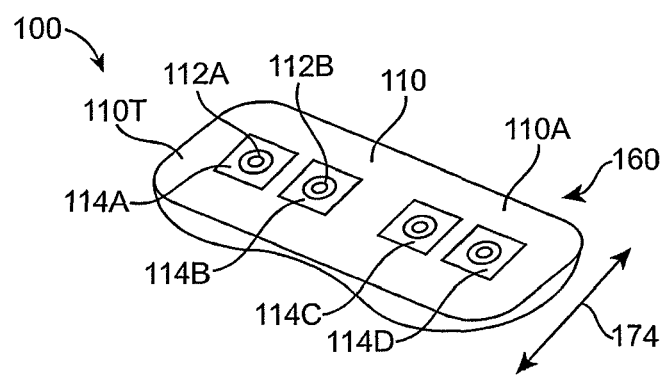
FIG. 1H shown a bottom isometric view of the adherent device as in FIGS. 1A to 1G.
Figure 1G:
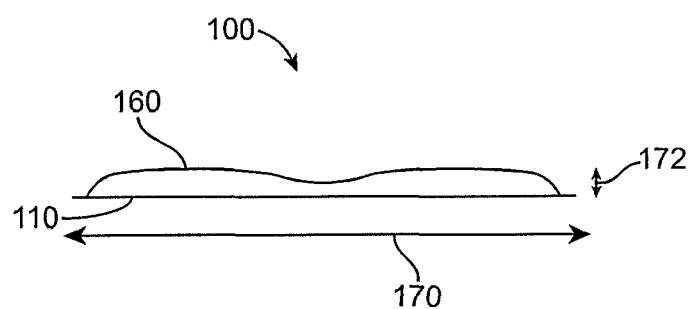
FIG. 1G shows a side view of the adherent device as in FIGS. 1A to 1F.

FIG. 1G shows a side view of adherent device 100 as in FIGS. 1A to 1F. Adherent device 100 comprises a maximum dimension, for example a length 170 from about 4 to 10 inches (from about 100 mm to about 250 mm), for example from about 6 to 8 inches (from about 150 mm to about 200 mm). In some embodiments, length 170 may be no more than about 6 inches (no more than about 150 mm). Adherent device 100 comprises a thickness 172. Thickness 172 may comprise a maximum thickness along a profile of the device. Thickness 172 can be from about 0.2 inches to about 0.6 inches (from about 5 mm to about 15 mm), from about 0.2 inches to about 0.4 inches (from about 5 mm to about 10 mm), for example about 0.3 inches (about 7.5 mm).

FIG. 1H shown a bottom isometric view of adherent device 100 as in FIGS. 1A to 1G. Adherent device 100 comprises a width 174, for example a maximum width along a width profile of adherent device 100. Width 174 can be from about 2 to about 4 inches (from about 50 mm to 100 mm), for example about 3 inches (about 75 mm).

Figure 1J:
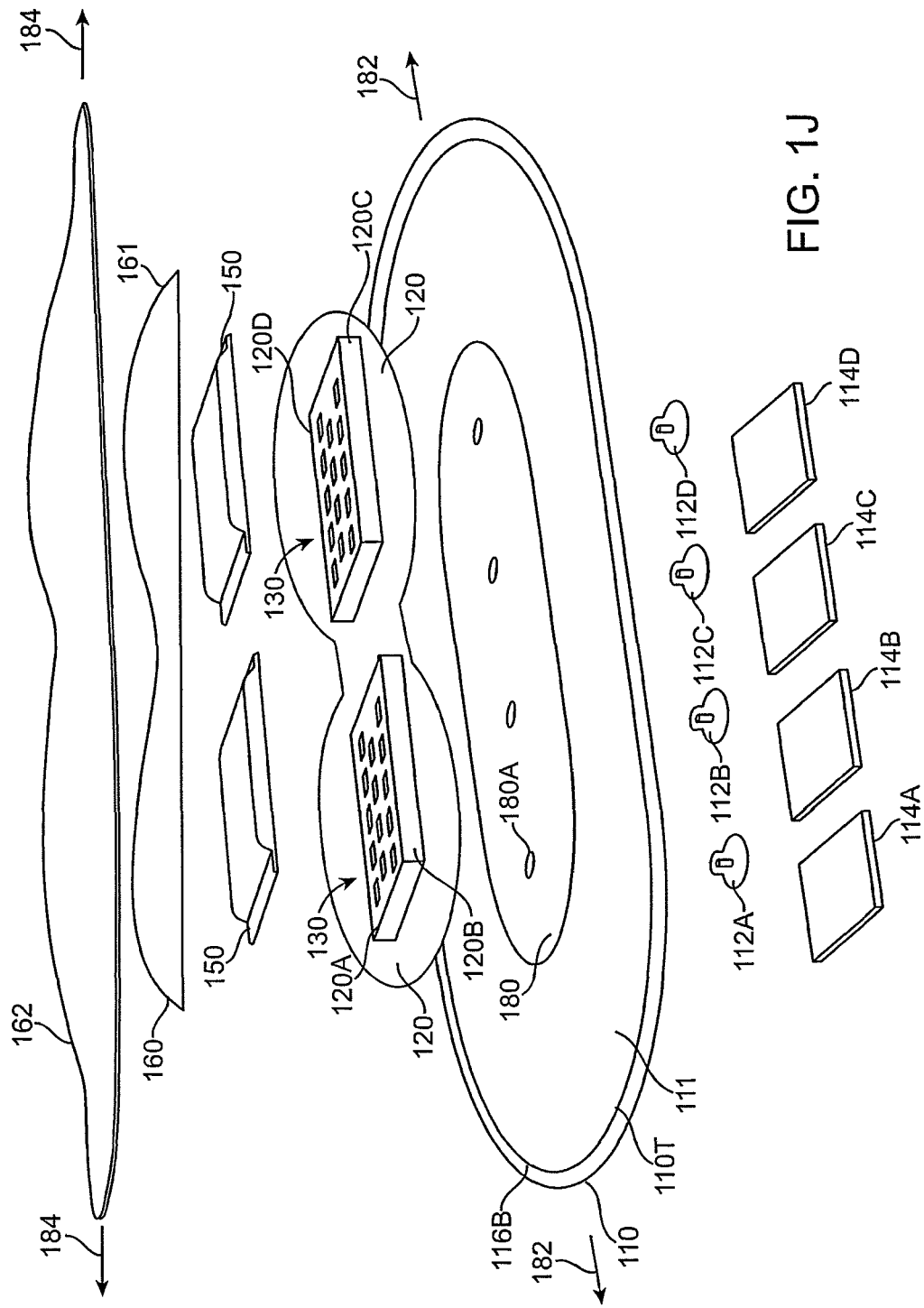

FIGS. 1I and 1J show a side cross-sectional view and an exploded view, respectively, of adherent device 100 as in FIGS. 1A to 1H. Device 100 comprises several layers. Gel 114A, or gel layer, is positioned on electrode 112A to provide electrical conductivity between the electrode and the skin. Electrode 112A may comprise an electrode layer. Adherent patch 110 may comprise a layer of breathable tape 110T, for example a known breathable tape, such as tricot-knit polyester fabric. An adhesive 116A, for example a layer of acrylate pressure sensitive adhesive, can be disposed on underside 110A of adherent patch 110.

FIGS. 1I1 and 1J1 show a side cross-sectional view and an exploded view, respectively, of embodiments of the adherent device with a temperature sensor affixed to the gel cover. In these embodiments, gel cover 180 extends over a wider area than in the embodiments shown in FIGS. 1I and 1J. Temperature sensor 177 is disposed over a peripheral portion of gel cover 180. Temperature sensor 177 can be affixed to gel cover 180 such that the temperature sensor can move when the gel cover stretches and tape stretch with the skin of the patient. Temperature sensor 177 may be coupled to temperature sensor circuitry 144 through a flex connection comprising at least one of wires, shielded wires, non-shielded wires, a flex circuit, or a flex PCB. This coupling of the temperature sensor allows the temperature near the skin to be measured though the breathable tape and the gel cover. The temperature sensor can be affixed to the breathable tape, for example through a cutout in the gel cover with the temperature sensor positioned away from the gel pads. A heat flux sensor can be positioned near the temperature sensor, for example to measure heat flux through to the gel cover, and the heat flux sensor coupled to heat flux circuitry similar to the temperature sensor.

The adherent device comprises electrodes 112A1, 112B1, 112C1 and 112D1 configured to couple to tissue through apertures in the breathable tape 110T. Electrodes 112A1, 112B1, 112C1 and 112D1 can be fabricated in many ways. For example, electrodes 112A1, 112B1, 112C1 and 112D1 can be printed on a flexible connector 112F, such as silver ink on polyurethane. Breathable tape 110T comprise apertures 180A1, 180B1, 180C1 and 180D1. Electrodes 112A1, 112B1, 112C1 and 112D1 are exposed to the gel through apertures 180A1, 180B1, 180C1 and 180D1 of breathable tape 110T. Gel 114A, gel 114B, gel 114C and gel 114D can be positioned over electrodes 112A1, 112B1, 112C1 and 112D1 and the respective portions of breathable tape 110T proximate apertures 180A1, 180B1, 180C1 and 180D1, so as to couple electrodes 112A1, 112B1, 112C1 and 112D1 to the skin of the patient. The flexible connector 112F comprising the electrodes can extend from under the gel cover to the printed circuit board to connect to the printed circuit boards and/or components supported thereon. For example, flexible connector 112F may comprise flexible connector 122A to provide strain relief, as described above.

In many embodiments, gel 114A, or gel layer, comprises a hydrogel that is positioned on electrode 112A to provide electrical conductivity between the electrode and the skin. In many embodiments, gel 114A comprises a hydrogel that provides a conductive interface between skin and electrode, so as to reduce impedance between electrode/skin interface. In many embodiments, gel may comprise water, glycerol, and electrolytes, pharmacological agents, such as beta blockers, ace inhibitors, diuretics, steroid for inflammation, antibiotic, antifungal agent. In specific embodiments the gel may comprise cortisone steroid. The gel layer may comprise many shapes, for example, square, circular, oblong, star shaped, many any polygon shapes. In specific embodiments, the gel layer may comprise at least one of a square or circular geometry with a dimension in a range from about 0.005" to about 0.100", for example within a range from about 0.015"-0.070", in some embodiments within a range from about 0.015"-0.040", and in specific embodiments within a range from about 0.020"-0.040". In many embodiments, the gel layer of each electrode comprises an exposed surface area to contact the skin within a range from about 100 mm^2 to about 1500 mm^2, for example a range from about 250 mm^2 to about 750 mm^2, and in specific embodiments within a range from about 350 mm^2 to about 650 mm^2. Work in relation with embodiments of the present invention suggests that such dimensions and/or exposed surface areas can provide enough gel area for robust skin interface without excessive skin coverage. In many embodiments, the gel may comprise an adhesion to skin, as may be tested with a 1800 degree peel test on stainless steel, of at least about 3 oz/in, for example an adhesion within a range from about 5-10 oz/in. In many embodiments, a spacing between gels is at least about 5 mm, for example at least about 10 mm. Work in relation to embodiments of the present invention suggests that this spacing may inhibit the gels from running together so as to avoid crosstalk between the electrodes. In many embodiments, the gels comprise a water content within a range from about 20% to about 30%, a volume resistivity within a range from about 500 to 2000 ohm-cm, and a pH within a range from about 3 to about 5.

In many embodiments, the electrodes, for example electrodes 112A to 112D, may comprise an electrode layer. A 0.001"-0.005" polyester strip with silver ink for traces can extend to silver/silver chloride electrode pads. In many embodiments, the electrodes can provide electrical conduction through hydrogel to skin, and in some embodiments may be coupled directly to the skin. Although at least 4 electrodes are shown, some embodiments comprise at least two electrodes, for example 2 electrodes. In some embodiments, the electrodes may comprise at least one of carbon-filled ABS plastic, silver, nickel, or electrically conductive acrylic tape. In specific embodiments, the electrodes may comprise at least one of carbon-filled ABS plastic, Ag/AgCl. The electrodes may comprise many geometric shapes to contact the skin, for example at least one of square, circular, oblong, star shaped, polygon shaped, or round. In specific embodiments, a dimension across a width of each electrodes is within a range from about 002" to about 0.050", for example from about 0.010 to about 0.040". In many a surface area of the electrode toward the skin of the patient is within a range from about 25 mm^2 to about 1500 mm^2, for example from about 75 mm^2 to about 150 mm^2. In many embodiments, the electrode comprises a tape that may cover the gel near the skin of the patient. In specific embodiments, the two inside electrodes may comprise force, or current electrodes, with a center to center spacing within a range from about 20 to about 50 mm. In specific embodiments, the two outside electrodes may comprise measurement electrodes, for example voltage electrodes, and a center-center spacing between adjacent voltage and current electrodes is within a range from about 15 mm to about 35 mm. Therefore, in many embodiments, a spacing between inner electrodes may be greater than a spacing between an inner electrode and an outer electrode.

In many embodiments, adherent patch 110 may comprise a layer of breathable tape 110T, for example a known breathable tape, such as tricot-knit polyester fabric. In many embodiments, breathable tape 110T comprises a backing material, or backing 111, with an adhesive. In many embodiments, the patch adheres to the skin of the patient's body, and comprises a breathable material to allow moisture vapor and air to circulate to and from the skin of the patient through the tape. In many embodiments, the backing is conformable and/or flexible, such that the device and/or patch does not become detached with body movement. In many embodiments, backing can sufficiently regulate gel moisture in absence of gel cover. In many embodiments, adhesive patch may comprise from 1 to 2 pieces, for example 1 piece. In many embodiments, adherent patch 110 comprises pharmacological agents, such as at least one of beta blockers, ace inhibitors, diuretics, steroid for inflammation, antibiotic, or antifungal agent. In specific embodiments, patch 110 comprises cortisone steroid. Patch 110 may comprise many geometric shapes, for example at least one of oblong, oval, butterfly, dogbone, dumbbell, round, square with rounded corners, rectangular with rounded corners, or a polygon with rounded corners. In specific embodiments, a geometric shape of patch 110 comprises at least one of an oblong, an oval or round. In many embodiments, the geometric shape of the patch comprises a radius on each corner that is no less than about one half a width and/or diameter of tape. Work in relation to embodiments of the present invention suggests that rounding the corner can improve adherence of the patch to the skin for an extended period of time because sharp corners, for example right angle corners, can be easy to peel. In specific embodiments, a thickness of adherent patch 110 is within a range from about 0.001" to about 0.020", for example within a range from about 0.005" to about 0.010". Work in relation to embodiments of the present invention indicates that these ranges of patch thickness can improve adhesion of the device to the skin of the patient for extended periods as a thicker adhesive patch, for example tape, may peel more readily. In many embodiments, length 170 of the patch is within a range from about 2" to about 10", width 174 of the patch is within a range from about 1" to about 5". In specific embodiments, length 170 is within a range from about 4" to about 8" and width 174 is within a range from about 2" to about 4". In many embodiments, an adhesion to the skin, as measured with a 180 degree peel test on stainless steel, can be within a range from about 10 to about 100 oz/in width, for example within a range from about 30 to about 70 oz/in width. Work in relation to embodiments of the present invention suggests that adhesion within these ranges may improve the measurement capabilities of the patch because if the adhesion is too low, patch will not adhere to the skin of the patient for a sufficient period of time and if the adhesion is too high, the patch may cause skin irritation upon removal. In many embodiments adherent patch 110 comprises a moisture vapor transmission rate (MVTR, g/m^2/24 hrs) per American Standard for Testing and Materials E-96 (ASTM E-96) is at least about 400, for example at least about 1000. Work in relation to embodiments of the present invention suggest that MVTR values as specified above can provide improved comfort, for example such that in many embodiments skin does not itch. In some embodiments, the breathable tape 110T of adherent patch 110 may comprise a porosity (sec./100 cc/in$^2$) within a wide range of values, for example within a range from about 0 to about 200. The porosity of breathable tape 110T may be within a range from about 0 to about 5. The above amounts of porosity can minimize itching of the patient's skin when the patch is positioned on the skin of the patient. In many embodiments, the MVTR values above may correspond to a MVTR through both the gel cover and the breathable tape. The above MVTR values may also correspond to an MVTR through the breathable tape, the gel cover and the breathable cover. The MVTR can be selected to minimize patient discomfort, for example itching of the patient's skin.

In some embodiments, the breathable tape may contain and elute a pharmaceutical agent, such as an antibiotic, anti-inflammatory or antifungal agent, when the adherent device is placed on the patient.

In many embodiments, tape 110T of adherent patch 110 may comprise backing material, or backing 111, such as a fabric configured to provide properties of patch 110 as described above. In many embodiments backing 111 provides structure to breathable tape 110T, and many functional properties of breathable tape 110T as described above. In many embodiments, backing 111 comprises at least one of polyester, polyurethane, rayon, nylon, breathable plastic film; woven, nonwoven, spun lace, knit, film, or foam. In specific embodiments, backing 111 may comprise polyester tricot knit fabric. In many embodiments, backing 111 comprises a thickness within a range from about 0.0005" to about 0.020", for example within a range from about 0.005" to about 0.010".

In many embodiments, an adhesive 116A, for example breathable tape adhesive comprising a layer of acrylate pressure sensitive adhesive, can be disposed on underside 110A of patch 110. In many embodiments, adhesive 116A adheres adherent patch 110 comprising backing 111 to the skin of the patient, so as not to interfere with the functionality of breathable tape, for example water vapor transmission as described above. In many embodiments, adhesive 116A comprises at least one of acrylate, silicone, synthetic rubber, synthetic resin, hydrocolloid adhesive, pressure sensitive adhesive (PSA), or acrylate pressure sensitive adhesive. In many embodiments, adhesive 116A comprises a thickness from about 0.0005" to about 0.005", in specific embodiments no more than about 0.003". Work in relation to embodiments of the present invention suggests that these thicknesses can allow the tape to breathe and/or transmit moisture, so as to provide patient comfort.

A gel cover 180, or gel cover layer, for example a polyurethane non-woven tape, can be positioned over patch 110 comprising the breathable tape. A PCB layer, for example flex printed circuit board 120, or flex PCB layer, can be positioned over gel cover 180 with electronic components 130 connected and/or mounted to flex printed circuit board 120, for example mounted on flex PCB so as to comprise an electronics layer disposed on the flex PCB layer. In many embodiments, the adherent device may comprise a segmented inner component, for example the PCB may be segmented to provide at least some flexibility. In many embodiments, the electronics layer may be encapsulated in electronics housing 160 which may comprise a waterproof material, for example silicone or epoxy. In many embodiments, the electrodes are connected to the PCB with a flex connection, for example trace 123A of flex printed circuit board 120, so as to provide strain relive between the electrodes 112A, 112B, 112C and 112D and the PCB.

Gel cover 180 can inhibit flow of gel 114A and liquid. In many embodiments, gel cover 180 can inhibit gel 114A from seeping through breathable tape 110T to maintain gel integrity over time. Gel cover 180 can also keep external moisture from penetrating into gel 114A. For example gel cover 180 can keep liquid water from penetrating though the gel cover into gel 114A, while allowing moisture vapor from the gel, for example moisture vapor from the skin, to transmit through the gel cover. The gel cover may comprise a porosity at least 200 sec./100 cc/in$^2$, and this porosity can ensure that there is a certain amount of protection from external moisture for the hydrogel.

In many embodiments, the gel cover can regulate moisture of the gel near the electrodes so as to keeps excessive moisture, for example from a patient shower, from penetrating gels near the electrodes. In many embodiments, the gel cover may avoid release of excessive moisture form the gel, for example toward the electronics and/or PCB modules. Gel cover 180 may comprise at least one of a polyurethane, polyethylene, polyolefin, rayon, PVC, silicone, non-woven material, foam, or a film. In many embodiments gel cover 180 may comprise an adhesive, for example a acrylate pressure sensitive adhesive, to adhere the gel cover to adherent patch 110. In specific embodiments gel cover 180 may comprise a polyurethane film with acrylate pressure sensitive adhesive. In many embodiments, a geometric shape of gel cover 180 comprises at least one of oblong, oval, butterfly, dogbone, dumbbell, round, square, rectangular with rounded corners, or polygonal with rounded corners. In specific embodiments, a geometric shape of gel cover 180 comprises at least one of oblong, oval, or round. In many embodiments, a thickness of gel cover is within a range from about 0.0005" to about 0.020", for example within a range from about 0.0005 to about 0.010". In many embodiments, gel cover 180 can extend outward from about 0-20 mm from an edge of gels, for example from about 5-15 mm outward from an edge of the gels.

In many embodiments, the breathable tape of adherent patch 110 comprises a first mesh with a first porosity and gel cover 180 comprises a breathable tape with a second porosity, in which the second porosity is less than the first porosity to inhibit flow of the gel through the breathable tape.

In many embodiments, device 100 includes a printed circuitry, for example a printed circuitry board (PCB) module that includes at least one PCB with electronics component mounted thereon on and the battery, as described above. In many embodiments, the PCB module comprises two rigid PCB modules with associated components mounted therein, and the two rigid PCB modules are connected by flex circuit, for example a flex PCB. In specific embodiments, the PCB module comprises a known rigid FR4 type PCB and a flex PCB comprising known polyimide type PCB. In specific embodiments, the PCB module comprises a rigid PCB with flex interconnects to allow the device to flex with patient movement. The geometry of flex PCB module may comprise many shapes, for example at least one of oblong, oval, butterfly, dogbone, dumbbell, round, square, rectangular with rounded corners, or polygon with rounded corners. In specific embodiments the geometric shape of the flex PCB module comprises at least one of dogbone or dumbbell. The PCB module may comprise a PCB layer with flex PCB 120 can be positioned over gel cover 180 and electronic components 130 connected and/or mounted to flex PCB 120 so as to comprise an electronics layer disposed on the flex PCB. In many embodiments, the adherent device may comprise a segmented inner component, for example the PCB, for limited flexibility. The printed circuit may comprise polyester film with silver traces printed thereon.

In many embodiments, the electronics layer may be encapsulated in electronics housing 160. Electronics housing 160 may comprise an encapsulant, such as a dip coating, which may comprise a waterproof material, for example silicone and/or epoxy. In many embodiments, the PCB encapsulant protects the PCB and/or electronic components from moisture and/or mechanical forces. The encapsulant may comprise silicone, epoxy, other adhesives and/or sealants. In some embodiments, the electronics housing may comprising metal and/or plastic housing and potted with aforementioned sealants and/or adhesives.

In many embodiments, the electrodes are connected to the PCB with a flex connection, for example trace 123A of flex PCB 120, so as to provide strain relive between the electrodes 112A, 112B, 112C and 112D and the PCB. In such embodiments, motion of the electrodes relative to the electronics modules, for example rigid PCB's 120A, 120B, 120C and 120D with the electronic components mounted thereon, does not compromise integrity of the electrode/hydrogel/skin contact. In some embodiments, the electrodes can be connected to the PCB and/or electronics module with a flex PCB 120, such that the electrodes and adherent patch can move independently from the PCB module. In many embodiments, the flex connection comprises at least one of wires, shielded wires, non-shielded wires, a flex circuit, or a flex PCB. In specific embodiments, the flex connection may comprise insulated, non-shielded wires with loops to allow independent motion of the PCB module relative to the electrodes.

In specific embodiments, cover 162 comprises at least one of polyester, 5-25% elastane/spandex, polyamide fabric; silicone, a polyester knit, a polyester knit without elastane, or a thermoplastic elastomer. In many embodiments cover 162 comprises at least 400% elongation. In specific embodiments, cover 162 comprises at least one of a polyester knit with 10-20% spandex or a woven polyamide with 10-20% spandex. In many embodiments, cover 162 comprises a water repellent coating and/or layer on outside, for example a hydrophobic coating, and a hydrophilic coating on inside to wick moisture from body. In many embodiments the water repellent coating on the outside comprises a stain resistant coating. Work in relation to embodiments of the present invention suggests that these coatings can be important to keep excessive moisture from the gels near the electrodes and to remove moisture from body so as to provide patient comfort.

In many embodiments, cover 162 can encase the flex PCB and/or electronics and can be adhered to at least one of the electronics, the flex PCB or adherent patch 110, so as to protect at least the electronics components and the PCB. Cover 162 can attach to adherent patch 110 with adhesive 116B. Cover 162 can comprise many known biocompatible cover materials, for example silicone. Cover 162 can comprise an outer polymer cover to provide smooth contour without limiting flexibility. In many embodiments, cover 162 may comprise a breathable fabric. Cover 162 may comprise many known breathable fabrics, for example breathable fabrics as described above. In some embodiments, the breathable cover may comprise a breathable water resistant cover. In some embodiments, the breathable fabric may comprise polyester, nylon, polyamide, and/or elastane (Spandex™) to allow the breathable fabric to stretch with body movement. In some embodiments, the breathable tape may contain and elute a pharmaceutical agent, such as an antibiotic, anti-inflammatory or antifungal agent, when the adherent device is placed on the patient.

The breathable cover 162 and adherent patch 110 comprise breathable tape can be configured to couple continuously for at least one week the at least one electrode to the skin so as to measure breathing of the patient. The breathable tape may comprise the stretchable breathable material with the adhesive and the breathable cover may comprises a stretchable breathable material connected to the breathable tape, as described above, such that both the adherent patch and cover can stretch with the skin of the patient. The breathable cover may also comprise a water resistant material. Arrows 182 show stretching of adherent patch 110, and the stretching of adherent patch can be at least two dimensional along the surface of the skin of the patient. As noted above, connectors 122A, 122B, 122C and 122D between PCB 130 and electrodes 112A, 112B, 112C and 112D may comprise insulated wires that provide strain relief between the PCB and the electrodes, such that the electrodes can move with the adherent patch as the adherent patch comprising breathable tape stretches. Arrows 184 show stretching of cover 162, and the stretching of the cover can be at least two dimensional along the surface of the skin of the patient.

Cover 162 can be attached to adherent patch 110 with adhesive 116B such that cover 162 stretches and/or retracts when adherent patch 110 stretches and/or retracts with the skin of the patient. For example, cover 162 and adherent patch 110 can stretch in two dimensions along length 170 and width 174 with the skin of the patient, and stretching along length 170 can increase spacing between electrodes. Stretching of the cover and adherent patch 110, for example in two dimensions, can extend the time the patch is adhered to the skin as the patch can move with the skin such that the patch remains adhered to the skin. Electronics housing 160 can be smooth and allow breathable cover 162 to slide over electronics housing 160, such that motion and/or stretching of cover 162 is slidably coupled with housing 160. The printed circuit board can be slidably coupled with adherent patch 110 that comprises breathable tape 110T, such that the breathable tape can stretch with the skin of the patient when the breathable tape is adhered to the skin of the patient, for example along two dimensions comprising length 170 and width 174.

The stretching of the adherent device 100 along length 170 and width 174 can be characterized with a composite modulus of elasticity determined by stretching of cover 162, adherent patch 110 comprising breathable tape 110T and gel cover 180. For the composite modulus of the composite fabric cover-breathable tape-gel cover structure that surrounds the electronics, the composite modulus may comprise no more than about 1 MPa, for example no more than about 0.3 MPa at strain of no more than about 5%. These values apply to any transverse direction against the skin.

The stretching of the adherent device 100 along length 170 and width 174, may also be described with a composite stretching elongation of cover 162, adherent patch 110 comprising breathable tape breathable tape 110T and gel cover 180. The composite stretching elongation may comprise a percentage of at least about 10% when 3 kg load is a applied, for example at least about 100% when the 3 kg load applied. These percentages apply to any transverse direction against the skin.

The printed circuit board may be adhered to the adherent patch 110 comprising breathable tape 110T at a central portion, for example a single central location, such that adherent patch 110 can stretch around this central region. The central portion can be sized such that the adherence of the printed circuit board to the breathable tape does not have a substantial effect of the modulus of the composite modulus for the fabric cover, breathable tape and gel cover, as described above. For example, the central portion adhered to the patch may be less than about 100 mm$^2$, for example with dimensions of approximately 10 mm by 10 mm (about 0.5" by 0.5"). Such a central region may comprise no more than about 10% of the area of patch 110, such that patch 110 can stretch with the skin of the patient along length 170 and width 174 when the patch is adhered to the patient.

The cover material may comprise a material with a low recovery, which can minimize retraction of the breathable tape from the pulling by the cover. Suitable cover materials with a low recovery include at least one of polyester or nylon, for example polyester or nylon with a loose knit. The recovery of the cover material may be within a range from about 0% recovery to about 25% recovery. Recovery can refer to the percentage of retraction the cover material that occurs after the material has been stretched from a first length to a second length. For example, with 25% recovery, a cover that is stretched from a 4 inch length to a 5 inch length will retract by 25% to a final length of 4.75 inches.

Electronics components 130 can be affixed to printed circuit board 120, for example with solder, and the electronics housing can be affixed over the PCB and electronics components, for example with dip coating, such that electronics components 130, printed circuit board 120 and electronics housing 160 are coupled together. Electronics components 130, printed circuit board 120, and electronics housing 160 are disposed between the stretchable breathable material of adherent patch 110 and the stretchable breathable material of cover 160 so as to allow the adherent patch 110 and cover 160 to stretch together while electronics components 130, printed circuit board 120, and electronics housing 160 do not stretch substantially, if at all. This decoupling of electronics housing 160, printed circuit board 120 and electronic components 130 can allow the adherent patch 110 comprising breathable tape to move with the skin of the patient, such that the adherent patch can remain adhered to the skin for an extended time of at least one week, for example two or more weeks.

An air gap 169 may extend from adherent patch 110 to the electronics module and/or PCB, so as to provide patient comfort. Air gap 169 allows adherent patch 110 and breathable tape 110T to remain supple and move, for example bend, with the skin of the patient with minimal flexing and/or bending of printed circuit board 120 and electronic components 130, as indicated by arrows 186. Printed circuit board 120 and electronics components 130 that are separated from the breathable tape 110T with air gap 169 can allow the skin to release moisture as water vapor through the breathable tape, gel cover, and breathable cover. This release of moisture from the skin through the air gap can minimize, and even avoid, excess moisture, for example when the patient sweats and/or showers.

The breathable tape of adherent patch 110 may comprise a first mesh with a first porosity and gel cover 180 may comprise a breathable tape with a second porosity, in which the second porosity is less than the first porosity to minimize, and even inhibit, flow of the gel through the breathable tape. The gel cover may comprise a polyurethane film with the second porosity.

Cover 162 may comprise many shapes. In many embodiments, a geometry of cover 162 comprises at least one of oblong, oval, butterfly, dogbone, dumbbell, round, square, rectangular with rounded corners, or polygonal with rounded corners. In specific embodiments, the geometric of cover 162 comprises at least one of an oblong, an oval or a round shape.

Cover 162 may comprise many thicknesses and/or weights. In many embodiments, cover 162 comprises a fabric weight: within a range from about 100 to about 200 g/m$^2$, for example a fabric weight within a range from about 130 to about 170 g/m$^2$.

In many embodiments, cover 162 can attach the PCB module to adherent patch 110 with cover 162, so as to avoid interaction of adherent patch 110C with the PCB having the electronics mounted therein. Cover 162 can be attached to breathable tape 110T and/or electronics housing 160 comprising over the encapsulated PCB. In many embodiments, adhesive 116B attaches cover 162 to adherent patch 110. In many embodiments, cover 162 attaches to adherent patch 110 with adhesive 116B, and cover 162 is adhered to the PCB module with an adhesive 161 on the upper surface of the electronics housing. Thus, the PCB module can be suspended above the adherent patch via connection to cover 162, for example with a gap 169 between the PCB module and adherent patch. In many embodiments, gap 169 permits air and/or water vapor to flow between the adherent patch and cover, for example through adherent patch 110 and cover 162, so as to provide patient comfort.

In many embodiments, adhesive 116B is configured such that adherent patch 110 and cover 162 can be breathable from the skin to above cover 162 and so as to allow moisture vapor and air to travel from the skin to outside cover 162. In many embodiments, adhesive 116B is applied in a pattern on adherent patch 110 such that the patch and cover can be flexible so as to avoid detachment with body movement. Adhesive 116B can be applied to upper side 110B of patch 110 and comprise many shapes, for example a continuous ring, dots, dashes around the perimeter of adherent patch 110 and cover 162. Adhesive 116B may comprise at least one of acrylate, silicone, synthetic rubber, synthetic resin, pressure sensitive adhesive (PSA), or acrylate pressure sensitive adhesive. Adhesive 16B may comprise a thickness within a range from about 0.0005" to about 0.005", for example within a range from about 0.001-0.005". In many embodiments, adhesive 116B comprises a width near the edge of patch 110 and/or cover 162 within a range from about 2 to about 15 mm, for example from about 3 to about 7 near the periphery. In many embodiments with such widths and/or thickness near the edge of the patch and/or cover, the tissue adhesion may be at least about 30 oz/in, for example at least about 40 oz/in, such that the cover remains attached to the adhesive patch when the patient moves.

In many embodiments, the cover is adhered to adherent patch 110 comprising breathable tape 110T at least about 1 mm away from an outer edge of adherent patch 110. This positioning protects the adherent patch comprising breathable tape 110T from peeling away from the skin and minimizes edge peeling, for example because the edge of the patch can be thinner. In some embodiments, the edge of the cover may be adhered at the edge of the adherent patch, such that the cover can be slightly thicker at the edge of the patch which may, in some instances, facilitate peeling of the breathable tape from the skin of the patient.

Gap 169 extend from adherent patch 110 to the electronics module and/or PCB a distance within a range from about 0.25 mm to about 4 mm, for example within a range from about 0.5 mm to about 2 mm.

In many embodiments, the adherent device comprises a patch component and at least one electronics module. The patch component may comprise adherent patch 110 comprising the breathable tape with adhesive coating 116A, at least one electrode, for example electrode 114A and gel 114. The at least one electronics module can be separable from the patch component. In many embodiments, the at least one electronics module comprises the flex printed circuit board 120, electronic components 130, electronics housing 160 and cover 162, such that the flex printed circuit board, electronic components, electronics housing and cover are reusable and/or removable for recharging and data transfer, for example as described above. In many embodiments, adhesive 116B is coated on upper side 110A of adherent patch 110B, such that the electronics module can be adhered to and/or separated from the adhesive component. In specific embodiments, the electronic module can be adhered to the patch component with a releasable connection, for example with Velcro™, a known hook and loop connection, and/or snap directly to the electrodes. Two electronics modules can be provided, such that one electronics module can be worn by the patient while the other is charged, as described above. Monitoring with multiple adherent patches for an extended period is described in U.S. Pat. App. No. 60/972,537, the full disclosure of which has been previously incorporated herein by reference. Many patch components can be provided for monitoring over the extended period. For example, about 12 patches can be used to monitor the patient for at least 90 days with at least one electronics module, for example with two reusable electronics modules.

In many embodiments, the adherent device comprises a patch component and at least one electronics module. The patch component may comprise adherent patch 110 comprising the breathable tape with adhesive coating 116A, at least one electrode, for example electrode 114A and gel 114. The at least one electronics module can be separable from the patch component. In many embodiments, the at least one electronics module comprises the flex printed circuit board 120, electronic components 130, electronics housing 160 and cover 162, such that the flex printed circuit board, electronic components, electronics housing and cover are reusable and/or removable for recharging and data transfer, for example as described above. In many embodiments, adhesive 116B is coated on upper side 110A of adherent patch 110B, such that the electronics module can be adhered to and/or separated from the adhesive component. In specific embodiments, the electronic module can be adhered to the patch component with a releasable connection, for example with Velcro™, a known hook and loop connection, and/or snap directly to the electrodes. Two electronics modules can be provided, such that one electronics module can be worn by the patient while the other is charged, as described above. Monitoring with multiple adherent patches for an extended period is described in U.S. Pat. App. No. 60/972,537, the full disclosure of which has been previously incorporated herein by reference. Many patch components can be provided for monitoring over the extended period. For example, about 12 patches can be used to monitor the patient for at least 90 days with at least one electronics module, for example with two reusable electronics modules.

At least one electrode 112A can extend through at least one aperture 180A in the breathable tape 110 and gel cover 180.

In some embodiments, the adhesive patch may comprise a medicated patch that releases a medicament, such as antibiotic, beta-blocker, ACE inhibitor, diuretic, or steroid to reduce skin irritation. The adhesive patch may comprise a thin, flexible, breathable patch with a polymer grid for stiffening. This grid may be anisotropic, may use electronic components to act as a stiffener, may use electronics-enhanced adhesive elution, and may use an alternating elution of adhesive and steroid.

FIG. 1K shows at least one electrode 190 configured to electrically couple to a skin of the patient through a breathable tape 192. In many embodiments, at least one electrode 190 and breathable tape 192 comprise electrodes and materials similar to those described above. Electrode 190 and breathable tape 192 can be incorporated into adherent devices as described above, so as to provide electrical coupling between the skin an electrode through the breathable tape, for example with the gel.

FIG. 2 shows a method 200 of monitoring a person.

A step 205 adheres a measurement device to patient to measure heart rate, activity, body posture, respiration rate and bioimpedance. The adherent device may comprise an adherent device as described above. The device may comprise ECG circuitry to measure the HR, an accelerometer to measure patient activity and orientation, impedance circuitry to measure breathing and patient hydration. Additional or alternative sensors can be used. For example, breathing may be determined with a sensor that provides a signal in response to expansion of the chest and expansion of the skin of the patient.

A step 210 measures, stores and processes patient data with adherent device. The adherent device may measure HR, patient activity and orientation, breathing and hydration, and these data can be stored on the adherent device, for example stored on the processor at least prior to communication with the gateway. The processor may determine a heart rate of the patient based on the ECG and may determine hydration and breathing based on an impedance signal from the impedance circuitry, for example.

A step 212 determines patient drug treatment. The drug treatment can be determined based on a prescription from a physician, for example.

A step 215 transmits patient data from adherent device to the gateway, as described above. A step 220 receives the patient data with the gateway.

A step 225 measures, stores and processes patient data with gateway. The gateway can store data of the adherent device and process the data. For example, the gateway can perform one or more of the steps of sub-steps so as to identify the CI. Also, the gateway may comprise at least one sensor to measure additional patient data, and may also combine data with data from additional measurement devices.

A step 230 transmits patient data from the gateway to the remote server.

A step 235 stores and processed patient data with remote server. The remoter server can store data of the adherent device and process the data. For example, the remote server can perform one or more of the steps of sub-steps so as to identify the CI.

A step 240 identifies functional CI with profile of remote heart rates. This functional CI can be identified in many ways, for example with one or more measurement of location of the heart rate data, measures of dispersion and variability of the heart rate data, skewness and kurtosis of the heart rate data, or comparison of portions around a mode of a single modal mounded distribution.

A sub-step 241—determines a profile of remote heart rates. A sub-step 242 determines a peak of the profile of remote heart rates. For example, the profile may comprise a histogram or Gaussian probability function and the peak may comprise the mode of the distribution or probability function. A sub-step 243 determines a portion of profile above peak. A sub-step 244 determines a portion of profile below peak. A sub-step 245 compares a portion above peak to a portion below peak. A sub-step 246 identifies functional CI when the portion above peak is less than portion below. For example, the portion above may correspond to the occurrence of heart rates above the peak hear rate and the portion below the peak may correspond to the occurrence of heart rates below the peak.

Based on the teachings described herein one can determine relevant parameters from the heart rate distribution profile so as to identify the functional CI.

A step 250 identifies functional CI with resting remote HR. A sub-step 251-determines the occurrence of heart rates corresponding to profile. A sub-step 252 determines a peak of the remote heart rates. A sub-step 254 determine the remote resting HR based on the peak of the remote HR. A sub-step 255 determines age corrected maximum HR. A sub-step 256 determines the HRR based on age corrected maximum HR and remote resting HR. A sub-step 257 identifies functional CI when the HRR is below the threshold.

A step 260 identifies functional CI with maximum HR. A sub-step 261 determines the threshold activity amount based on patient data from a plurality of other patients, for example from a patient population measured with substantially similar adherent devices when the patients are at home. A sub-step 262 determines the patient activity above threshold. A sub-step 263 determines heart rates of the patient corresponding to patient activity above threshold. For example, the heart rate of the patient may comprise a maximum HR of the patient and the maximum HR of the patient can be compared to the threshold. A sub-step 264 determines a correlation of HR above threshold with one or more of activity, body posture, respiration rate and bioimpedance. A sub-step 265 determines patient drug treatment and compliance. A sub-step 266 determines functional CI based on patient drug treatment and correlation of HR above threshold with the one or more of activity, body posture, respiration rate or bioimpedance. A step 270 transmits notification to one or more of physician or patient based on identification of CI.

The 85% cut-off for functional CI classification can be modified to other cut-offs to account for pharmacological modification of heart rate response such as beta-blockers and other chronotropic/lusitropic medication.

The processor system, as described above, may comprise instructions of a computer program embedded thereon so as to perform many of the steps of the method 200. For example, many of the steps of the method 200 can be performed with processor system comprising the processor of the adherent device, the processor of the gateway and the processor of the remote server. The method 200 can be performed with one or more of the processor of the adherent device, the processor of the gateway and the processor of the remote server. Further the steps of the method 200 can be distributed among the processor of the processor system such that each processor performs at least one of the steps or sub-steps of method 200.

It should be appreciated that the specific steps illustrated in FIG. 2 provide a particular method of monitoring a patient and responding to a signal event, in accordance with an embodiment of the present invention. Other sequences of steps may also be performed in accordance with alternative embodiments. For example, alternative embodiments of the present invention may perform the steps outlined above in a different order. Moreover, the individual steps illustrated in FIG. 2 may include multiple sub-steps that may be performed in various sequences as appropriate to the individual step. Alternatively, the multiple sub-steps may be performed as an individual step. Furthermore, additional steps may be added or removed depending on the particular applications. One of ordinary skill in the art would recognize many variations, modifications, and alternatives.

The patient data as described above can be combined to determine the functional CI of the patient. For example, the data can be combined with one or more correlations of heart rate to one or more of the activity index (hereinafter "AI"), body posture (hereinafter "BP"), impedance of the patient (hereinafter "BioZ" or respiration rate (hereinafter "RR"). The AI may comprise an index based on the measurements from the three axes of the accelerometer as described above. The BP may comprise an angle of the patient based on orientation from accelerometer as described above. The BioZ may comprise impedance averaged over patient breathing cycles to correct for patient breathing or corrected for patient breathing with a portion of the breathing pattern. For example, the heart rate can be correlated with these data with the equation:

$$HR = a*AI + b*BP + c*BioZ + d*RR,$$

where a, b, c and d are respective correlation coefficients. The above equation is merely an example of a correlation equation as many additional equations can be used such as equations with cross terms, for example of AI with BP, and with squared terms, for example with coefficients of (BP)*(BP).

The patient data may also be combined with multi-dimensional look up tables, for example with look up tables comprising levels or tiers for each measured data parameter such as AI. For example, AI may comprise a level, or tier, based on counts of an accelerometer or other index.

Embodiments as described herein can be incorporated with many commercially available patient monitoring and treatment systems such as the OptiVol™ alert algorithm and computer programs embodying instructions thereof commercially available from Medtronic, the CareLink™ server commercially available from Medtronic, the Latitude™ patient management system commercially available from Boston Scientific, the Merlin™ system commercially available from St. Jude and the MCOT™ commercially available from CardioNet.

Experimental Clinical Studies

An experimental clinical study can be conducted on an empirical number of patients to determine empirically parameters of the above described adherent device and processor system so as to determine functional CI of the patient. The empirically determined parameters can be used with programs of the processor system to determine status of the patient, for example to determine deterioration in the status, based on the teachings as described herein.

FIGS. 3A1 to 3A5 show heart rate, activity index, body posture, impedance, and respiration rate measured from an adherent device adhered to the skin of the patient. Although the device can be adhered for at least about one week as described above, the data of FIG. 3A show at least about 24 hours of measured data to show an example of data suitable for combination. Each of FIGS. 3A1 to 3A5 have a corresponding time base, for example from a data time stamp of the processor of the adherent device.

FIG. 3A1 shows the heart rate of the patient in beats per minute from 00:00 hours to 24:00 hours. The heart rate may be determined with one or more of the processor of the adherent device, the processor of the gateway or the processor of the remote server. The HR shows an elevation at about 11:00.

FIG. 3A2 shows patient activity amounts. The patient activity amounts may comprise an index and many measures of patient activity. For example, the activity index may comprise counts and/or an arbitrary scale, and the values can range from about 0 to about 300. The data show a peak at about 11:00.

FIG. 3A3 shows patient body posture angle. The patient body posture is shown to be upright, at around 80 degrees from about 07:00 to about 18:00. These data indicate that the patient is awake and upright from about 07:00 to about 18:00.

FIG. 3A4 shows patient impedance. The patient impedance is shown to vary from about 60 to about 80 Ohms. For example with local peaks around 11:00 and 14:00 corresponding to about 74 and 78 Ohms, respectively.

FIG. 3A5 shows patient breathing rate, also referred to as patient respiration rate. The respiration rate of the patient varies from about 10 breaths per minute to about 30 breaths per minute.

Based on the teachings described herein, the instruction of the processor system can identify functional CI from the HR data and data of one or more of the other sensors. The method and instructions of the processor system can identify functional CI of the patient based on HR and one or more sensors from about 10:00 to 11:00. For example, the patient activity comprises a peak around 11 am corresponding to an activity amount above the threshold determined with similar adherent devices from a population of patients or relative to the patient's own activity mean over a given 24 hour period. For example, the threshold may correspond to an activity amount of 100, such that the patient heart rates corresponding to the activity index above the threshold of 100 correspond to maximum HR of the patient. The processor system comprises patient data including the age of the patient such that the age corrected maximum HR can be determined and the functional CI of the patient can be identified based on the age corrected maximum HR and the maximum HR of the patient. The increase in activity was not paralleled by a comparable increase in HR so as to comprise a diagnostic marker to identify CI with the remote patient measurements as described herein.

The processor system and methods described herein can identify functional CI of the patient based on the profile of the HR data, for example based on histogram as described herein.

Figure 3C:
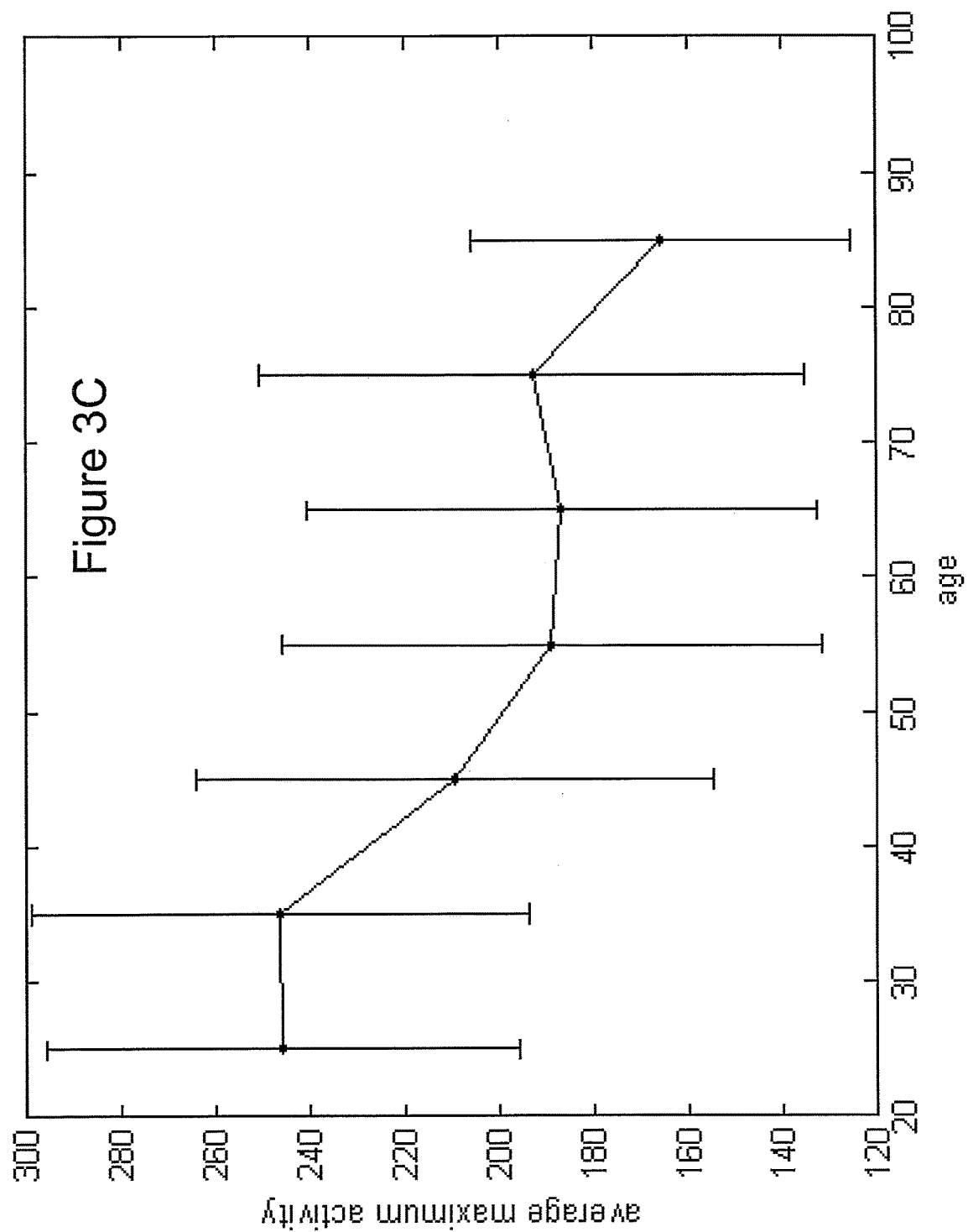
FIG. 3C shows average maximum activity of patients based on age for ages from about 20 to about 90.
Figure 3B:
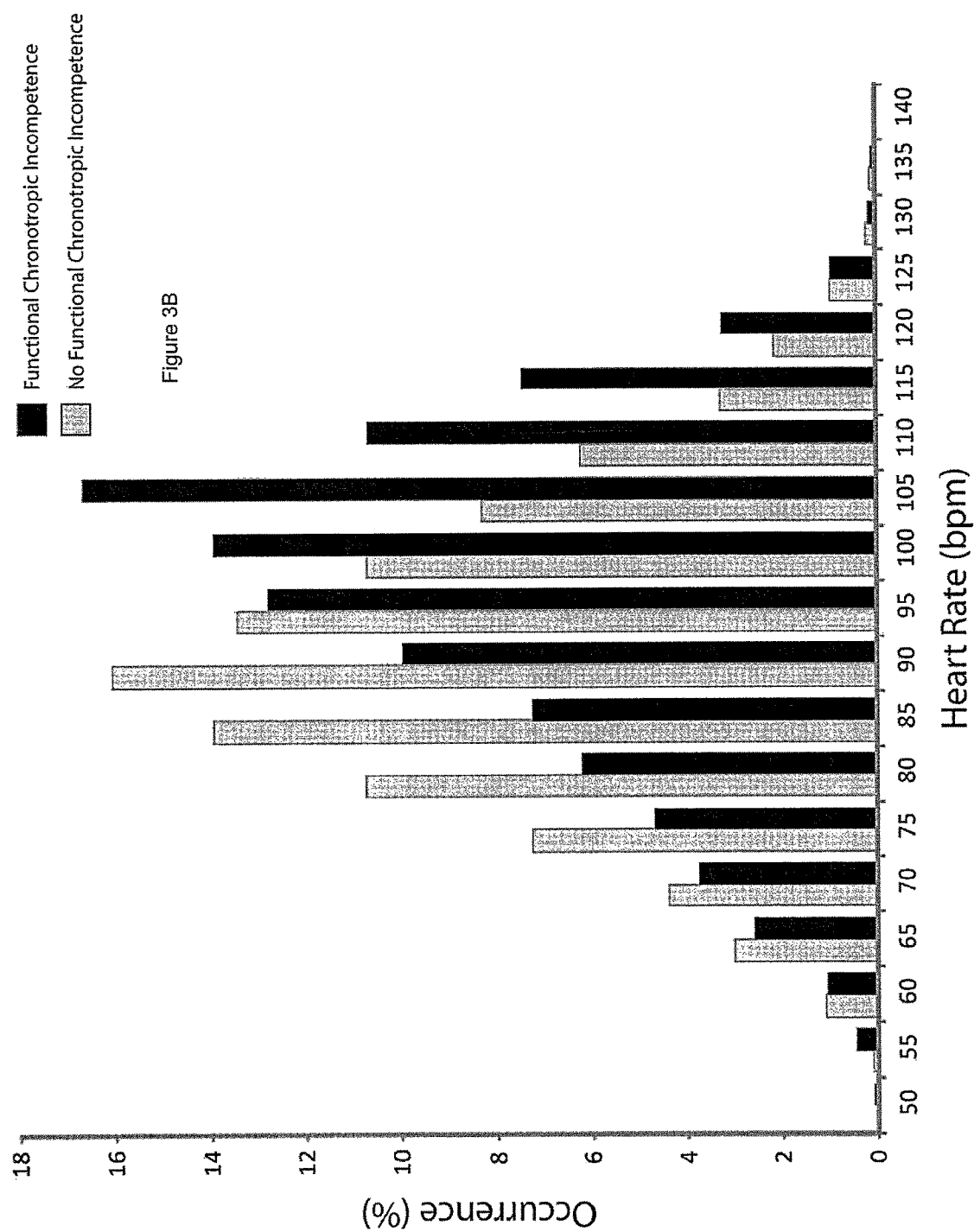
FIG. 3B shows measured patient heart rate profile data in accordance with embodiments of the present invention.

FIG. 3B shows patient data measured remotely with an adherent device as described above. The patient data shows a distribution comprising a histogram for a first patient without functional CI and a second patient with functional CI. The patient heart rate data may comprise data measured during the day when the patient is active. The data may comprise a modal heart rate distribution. The data show a histogram for each patient. The heart rate of each patient is determined over time. The occurrence of heart rate in 5 beat per minute intervals is shown from 50 beats per minute to 140 beats per minute. The patient with no functional CI shows a peak at about 90 beats per minute, and the patient with functional CI shows a peak at about 105 beats per minute.

The functional CI can be identified with the profile of remote heart rates. This functional CI can be identified in many ways, for example with one or more measurement of location of the heart rate data, measures of dispersion and variability of the heart rate data, skewness and kurtosis of the heart rate data, or comparison of portions around a mode of a single modal mounded distribution.

The histogram distribution of each patient comprises a first side corresponding to a first amount of occurrences of heart rates below the peak and a second side corresponding to a second amount of occurrences of heart rates above the peak. The distribution of the first patient without functional CI has a first amount of occurrences below the peak at 90 bpm and a second amount of occurrence above the peak at 90 bpm, and the first amount is substantially equal to the second amount. The distribution of the second patient with functional CI has a first amount of occurrences below the peak at 105 bpm and a second amount of occurrence above the peak at 105 bpm, and the first amount is substantially greater than the second amount.

Alternatively or in combination, the histogram distribution of each patient can be fit to a Gaussian distribution and a skew of the distribution for each patient determined. For example, the first patient without functional CI comprises substantially no skew of the histogram distribution, and the second patient with functional CI comprises significant skew of the histogram distribution.

The peak of the HR data of FIG. 3B corresponds to the resting HR of the patient, such that the HRR of the patient can be calculated. The HRR can be combined with the profile from the histogram to identify the patient CI.

FIG. 3C shows average maximum activity of patients based on age for ages from about 20 to about 90. These average maximum activity levels from a population of patients can be used to determine threshold criteria and correlate activity with additional measurement parameters, such has heart rate and change in heart rate.

Clinical Studies for Remote Monitoring and Diagnosis of Chronotropic Incompetence in HF patients.

A study can be conducted to diagnose functional CI during activities of daily living, through remote monitoring, so as to provide important information for effectively managing HF and understanding the role of functional CI in contributing to HF symptoms. The study may comprise HF patients having an ejection fraction (hereinafter "EF") of 40% or less.

Study Design: The study may comprise a prospective monitoring study of patients with chronic HF using an external multi-sensor monitor, for example an adherent monitor as described above. The study may comprise data from multiple centers and enroll approximately 200 enrolled patients with NYHA Class III/IV, EF≤40%. The wireless monitoring device can be applied to the patient's chest and replaced weekly during a 90-day monitoring period. Heart rate (HR), respiratory rate, activity level and body impedance data from the device were transmitted at regular interval via phone and used for offline analysis.

The data can be analyzed to determine results and compare the determined functional CI to similar study populations. The following can be determined for the population: gender, age, body mass index, EF, percentage of patient with beta-blockers. For each patient, the modal HR during daily activity was calculated and used to perform functional CI determination. The percentage of patients with functional CI can be determined when defined as an inability to reach 85% of age-predicted maximum HR. When adjusted for beta-blocker use, the percentage of patient having functional CI can be determined.

Applicants note that a study design as described above has been conducted on a population of approximately 300 patients.

FIG. 3D1 shows correlation of heart rate data with activity data for patients without functional CI from the study. The fit parameters are HR (bpm)=0.0985*(Activity)+75.4 ($R^2$=0.151)

FIG. 3D2 shows correlation of heart rate data with activity data for patients with functional CI from the study. The fit parameters are HR (bpm)=0.0126*(Activity)+82.651 ($R2$=0.0026)

The correlations shown in FIGS. 3D1 and 3D2 are examples of linear correlations of heart rate with activity that can be determined. The correlation coefficient of the patients without functional CI shows a steeper slope for a linear fit between HR and activity when compared to patients with functional CI. The less steep curve of the patients with CI shows a blunting of heart rate response to activities of daily living, when adjusted for age. This blunting of HR elevation can be combined with additional patient measurement data, as described above.

Applicants note that the presence of functional CI in the study was determined based on measured activity above a percentage of the mean age adjusted maximum heart rate as shown above with reference to FIG. 3C. This measured activity above the threshold amount can be used to determine the presence of functional CI. Based on this crossing of measured patient activity above the threshold and the corresponding HR can be used to identify the patient as having functional CI or not having functional CI. Of approximately 300 patients, about 29% of the patients were determined to have functional CI and approximately 12% were determined to have no functional CI. For the remaining 59% of the patients, the functional CI was indeterminate based on activity and heart rate due to the sedentary status of the patient. However, Applicants note that additional patient measurement data can be used to identify the functional CI in accordance with additional steps of method 300 described above, such that the presence (or absence) of functional CI can be positively determined for a majority of patients. For example the profile of the HR distribution and the heart rate reserve of the patient as measured at home can be used to determine the presence of functional CI.

Additional correlations and correspondence among patient data can be made with additional variables as described above so as to identify functional CI in a patient population. The correlations may comprise a plurality of variables correlated with the HR profile, as described above. Look up tables can also be determined to compare functional CI with measurement data such as activity, orientation, activity, respiration rate and body temperature.

While the exemplary embodiments have been described in some detail, by way of example and for clarity of understanding, those of skill in the art will recognize that a variety of modifications, adaptations, and changes may be employed. Hence, the scope of the present invention should be limited solely by the appended claims.

What is claimed is:

1. An apparatus to monitor a patient, the apparatus comprising,
a processor system comprising at least one processor having a tangible medium with instructions of a computer program embodied thereon, the processor system configured to:
receive heart rate data of the patient, the heart rate data comprising a plurality of measurements of the patient's heart rate taken over a period of time by an adherent and/or implantable device associated with the patient without subjecting the patient to a cardiac stress test;
construct a heart rate profile based on the plurality of measurements taken over a period of time, wherein a peak of the heart rate profile is selected as representative of the resting heart rate of the patient, the peak of the heart rate profile corresponding with a mode of the plurality of measurements;
determine an age-corrected maximum heart rate of the patient based on patient age;
determine a heart rate reserve (HRR) based on the age corrected maximum heart rate and resting heart rate of the patient; and
compare the HRR to a threshold value and identify chronotropic incompetence if the HRR is below the threshold.

2. The apparatus of claim 1, wherein the patient is remotely located with respect to a clinic.

3. A method of monitoring a patient to detect chronotropic incompetence, the method comprising:
receiving heart rate data of the patient, the heart rate data comprising a plurality of measurements of the patient's heart rate taken over a period of time by an adherent and/or implantable device associated with the patient without subjecting the patient to a cardiac stress test;
constructing a heart rate profile based on the plurality of heart rate measurements taken over a period of time, wherein a peak of the heart rate profile is selected as representative of the resting heart rate of the patient, the peak of the heart rate profile corresponding with a mode of the plurality of measurements;
determining an age-corrected maximum heart rate of the patient based on patient age;
determining a heart rate reserve (HRR) based on the age corrected maximum heart rate and resting heart rate of the patient; and
comparing the HRR to a threshold value and identifying chronotropic incompetence if the HRR is below the threshold.

4. The apparatus of claim 1,
wherein the processor system is further configured to:
receive activity data of the patient;
compare patient activity data to an activity threshold to determine activity above the activity threshold;
determine heart rate data corresponding with patient activity data above the activity threshold;
determine a maximum heart rate of the patient based on the heart rate data determined to correspond with patient activity data above the activity threshold; and
identify chronotropic incompetence based, at least in part, on a comparison of the maximum heart rate of the patient to a threshold maximum heart rate.

5. The apparatus of claim 4, wherein the processor further comprises instructions to determine a correlation of the maximum heart rate with one or more of the patient activity, patient body posture, patient breath rate or patient respiration rate and wherein the processor system is configured to identify chronotropic incompetence based on the correlation.

6. The apparatus of claim 4, wherein the activity threshold is determined based on a patient data received from a plurality of other patients.

7. The method of claim 3, further comprising:
receiving activity data of the patient;
comparing patient activity data to an activity threshold to determine activity above the activity threshold;
determining heart rate data corresponding with patient activity data above the activity threshold;
determining a maximum heart rate of the patient based on the heart rate data determined to correspond with patient activity data above the activity threshold; and identifying chronotropic incompetence based, at least in part, on a comparison of the maximum heart rate of the patient to a threshold maximum heart rate.

8. The method of claim 7, further comprising determining a correlation of the maximum heart rate with one or more of the patient activity, patient body posture, patient breath rate or patient respiration rate.

9. The method of claim 8, wherein identifying chronotropic incompetence is further based on the correlation.

10. The method of claim 7, wherein the activity threshold is determined based on a patient data received from a plurality of other patients.

* * * * *